(12) United States Patent
Horii et al.

(10) Patent No.: US 11,117,135 B2
(45) Date of Patent: Sep. 14, 2021

(54) LIQUID-SEALED CARTRIDGE AND LIQUID TRANSFERRING METHOD

(71) Applicants: SYSMEX CORPORATION, Kobe (JP); ASTI CORPORATION, Shizuoka (JP)

(72) Inventors: Kazuyoshi Horii, Kobe (JP); Takao Fujiwara, Kobe (JP); Tomoyuki Nose, Kobe (JP); Yasunori Maekawa, Kobe (JP); Noriyuki Ogai, Hamamatsu (JP); Yasuhiro Toda, Hamamatsu (JP)

(73) Assignees: Sysmex Corporation, Hyogo (JP); ASTI Corporation, Shizuoka (JP)

( * ) Notice: Subject to any disclaimer, the term of this patent is extended or adjusted under 35 U.S.C. 154(b) by 339 days.

(21) Appl. No.: 15/796,168

(22) Filed: Oct. 27, 2017

(65) Prior Publication Data

US 2018/0117583 A1    May 3, 2018

(30) Foreign Application Priority Data

Oct. 28, 2016  (JP) .............................. JP2016-211492

(51) Int. Cl.
*G01N 33/536* (2006.01)
*G01N 33/576* (2006.01)
(Continued)

(52) U.S. Cl.
CPC ........... *B01L 3/508* (2013.01); *B01L 3/50273* (2013.01); *B01L 3/502707* (2013.01);
(Continued)

(58) Field of Classification Search
USPC ......... 422/504, 506, 537–538, 502–503, 507
See application file for complete search history.

(56) References Cited

U.S. PATENT DOCUMENTS

| 7,964,161 B2 | 6/2011 | Kadel et al. |
| 8,703,070 B1 | 4/2014 | Parng et al. |

(Continued)

FOREIGN PATENT DOCUMENTS

| EP | 3023335 | 5/2016 |
| EP | 1289658 | 7/2017 |

(Continued)

OTHER PUBLICATIONS

The Communication pursuant to Article 94(3) EPC dated Mar. 29, 2019 in a counterpart European patent application No. 17197994.1.

(Continued)

*Primary Examiner* — Brian R Gordon

(57) ABSTRACT

Disclosed is a liquid-sealed cartridge in which a liquid is transferred by a centrifugal force generated when the liquid-sealed cartridge is rotated around a rotation shaft, including: a liquid storage portion configured to store the liquid therein; a seal having an outer peripheral portion connected to the liquid storage portion, the seal being configured to seal the liquid storage portion; a flow path connected to the liquid storage portion via the seal, through which the liquid in the liquid storage portion is transferred by the centrifugal force in a direction away from the rotation shaft, wherein, when the seal receives a pressing force, the seal is inclined in a pressing direction, with one portion of the outer peripheral portion thereof remaining connected with the liquid storage portion, and the other portion of the outer peripheral portion being separated from the liquid storage portion.

9 Claims, 17 Drawing Sheets

(51) Int. Cl.
*G01N 35/10* (2006.01)
*B01L 3/00* (2006.01)
*B01L 9/00* (2006.01)
*F16K 99/00* (2006.01)
*F16K 1/18* (2006.01)
*G01N 33/53* (2006.01)
*G01N 21/07* (2006.01)

(52) U.S. Cl.
CPC ......... *B01L 3/502738* (2013.01); *B01L 9/527* (2013.01); *F16K 1/18* (2013.01); *F16K 99/0015* (2013.01); *G01N 33/5304* (2013.01); *G01N 33/536* (2013.01); *G01N 33/5764* (2013.01); *G01N 35/10* (2013.01); *B01L 2200/06* (2013.01); *B01L 2200/0621* (2013.01); *B01L 2200/0684* (2013.01); *B01L 2300/047* (2013.01); *B01L 2300/0627* (2013.01); *B01L 2300/0803* (2013.01); *B01L 2300/123* (2013.01); *B01L 2300/1805* (2013.01); *B01L 2400/0409* (2013.01); *B01L 2400/0475* (2013.01); *B01L 2400/0638* (2013.01); *F16K 2099/0084* (2013.01); *G01N 21/07* (2013.01)

(56) References Cited

U.S. PATENT DOCUMENTS

| | | | |
|---|---|---|---|
| 10,697,989 B2* | 6/2020 | Horii | G01N 35/02 |
| 2002/0001848 A1 | 1/2002 | Bedingham et al. | |
| 2005/0093087 A1* | 5/2005 | Kadel | B01L 3/502738 |
| | | | 257/415 |
| 2006/0228256 A1* | 10/2006 | McDevitt | B01J 19/0046 |
| | | | 422/82.05 |
| 2006/0245972 A1 | 11/2006 | Osone et al. | |
| 2009/0074626 A1 | 3/2009 | Kadel et al. | |
| 2010/0243078 A1* | 9/2010 | Yoo | F16K 99/0001 |
| | | | 137/468 |

FOREIGN PATENT DOCUMENTS

| | | |
|---|---|---|
| JP | 2005-096866 | 4/2005 |
| JP | 2011-047709 | 3/2011 |

OTHER PUBLICATIONS

Office Action in Europe Application No. 17197994.1 dated Nov. 26, 2019, 4 pages.

* cited by examiner

FIG. 1A                                           EMBODIMENT 1
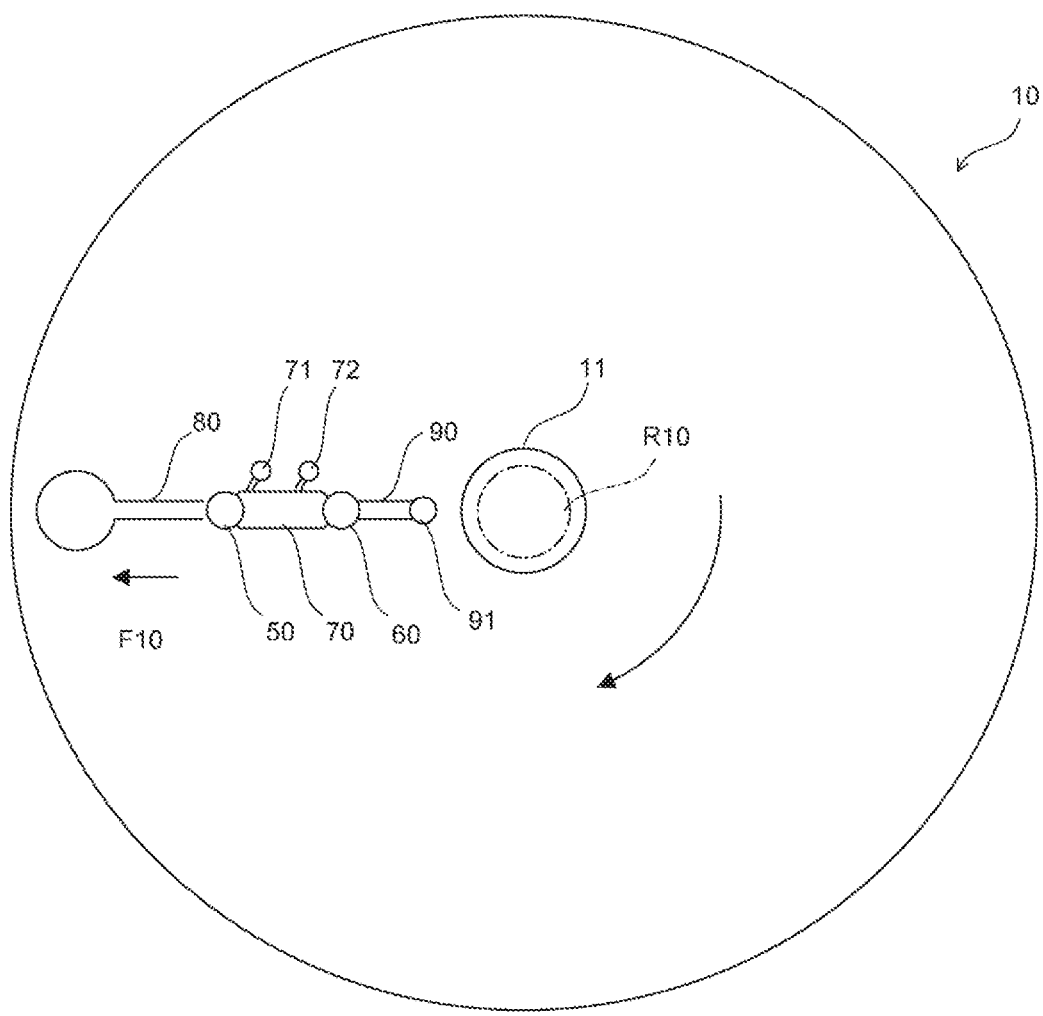
FIG. 1B
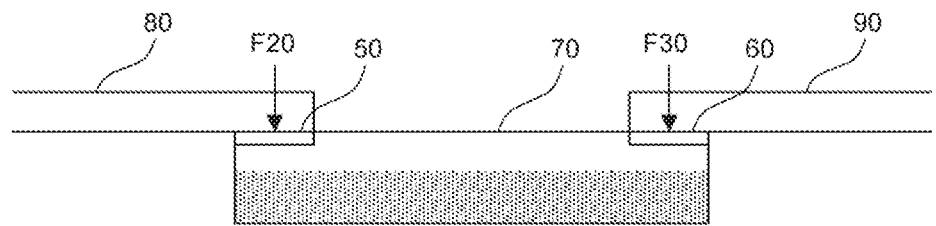
FIG. 1C
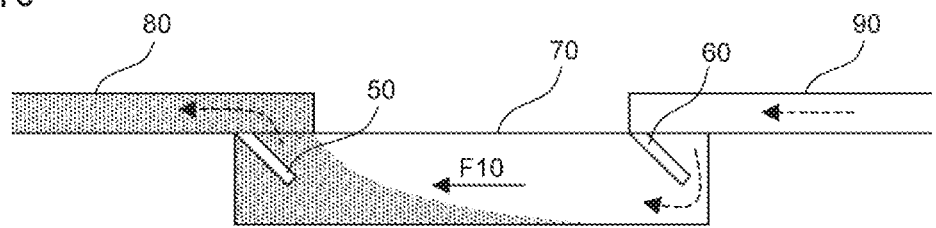

FIG. 7
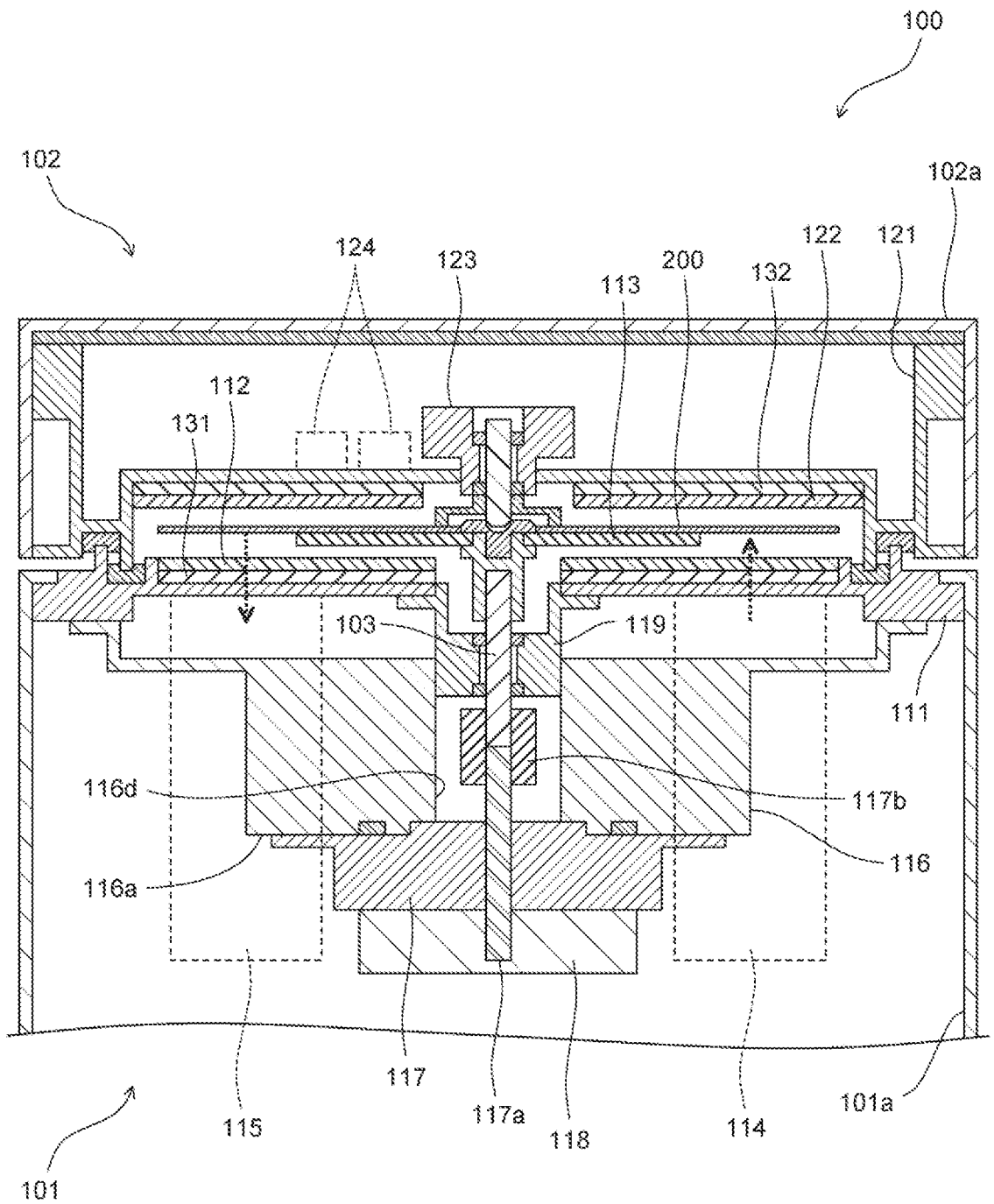

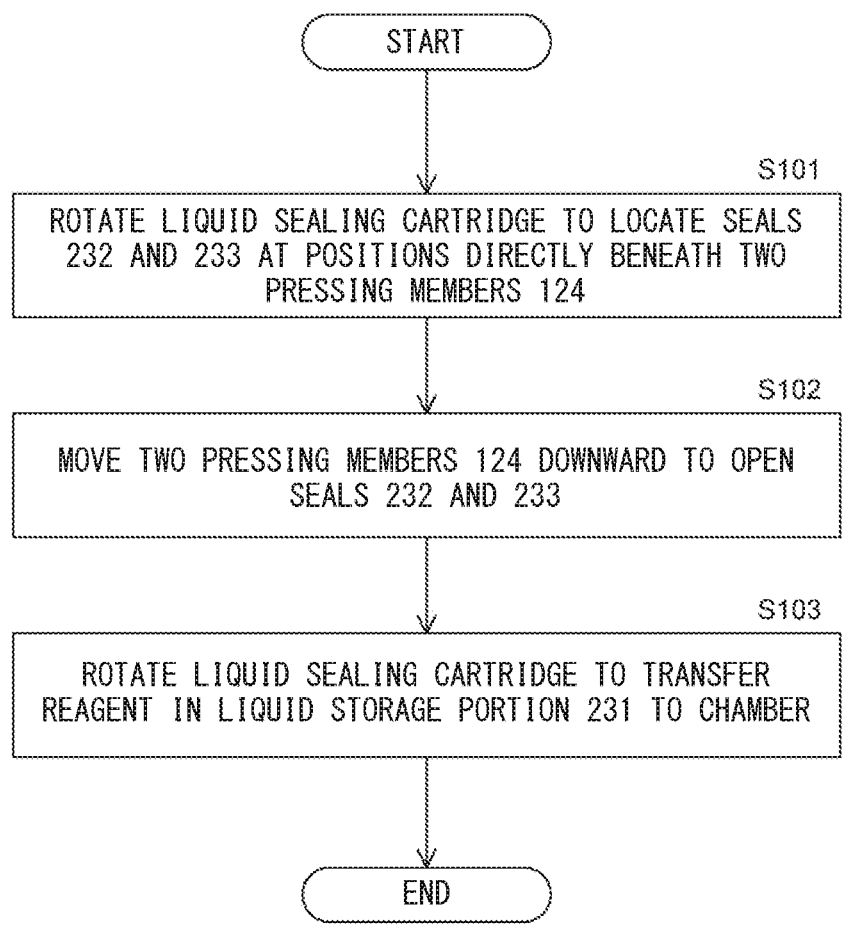

FIG. 11A  EMBODIMENT 2
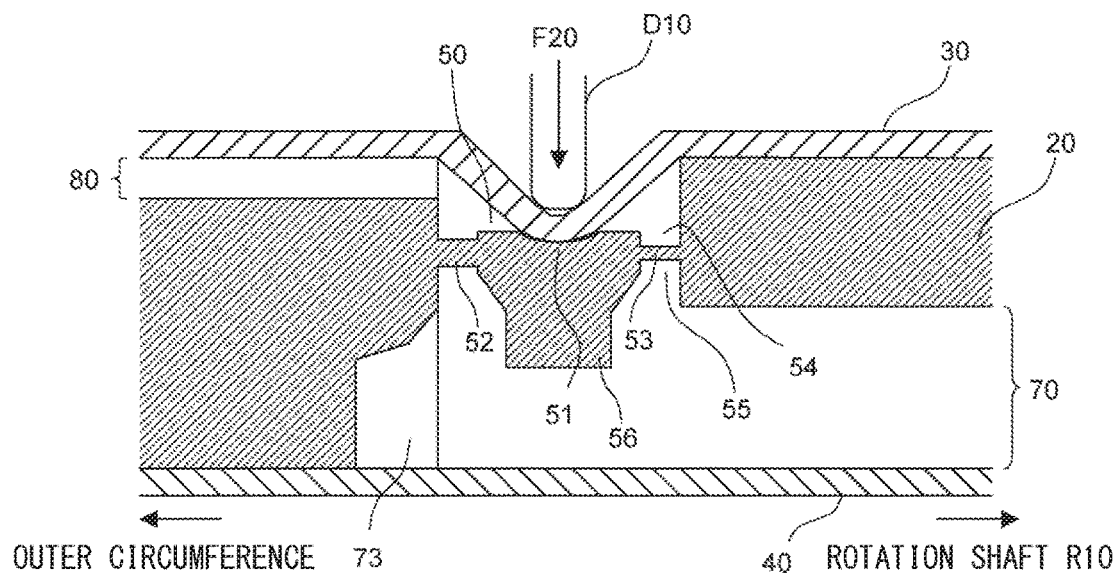
FIG. 11B
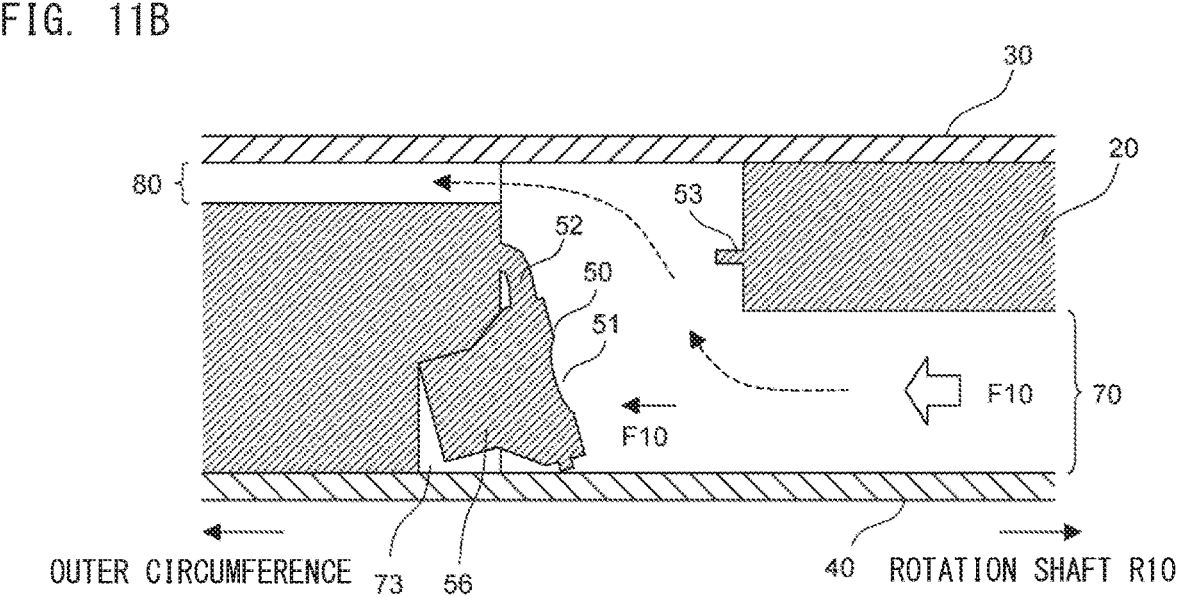

FIG. 12A                                                                    EMBODIMENT 3
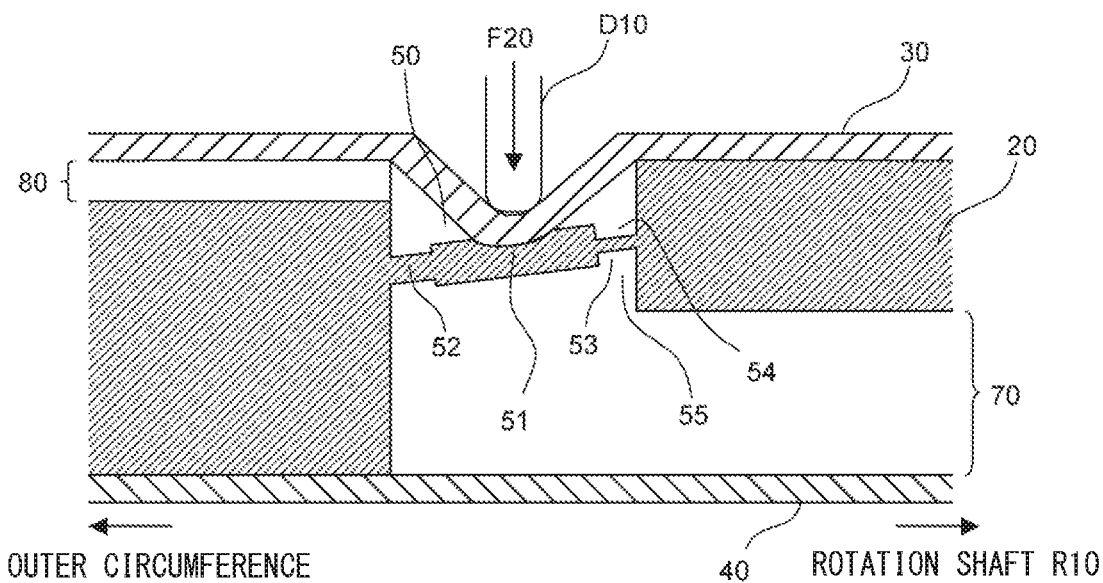
FIG. 12B
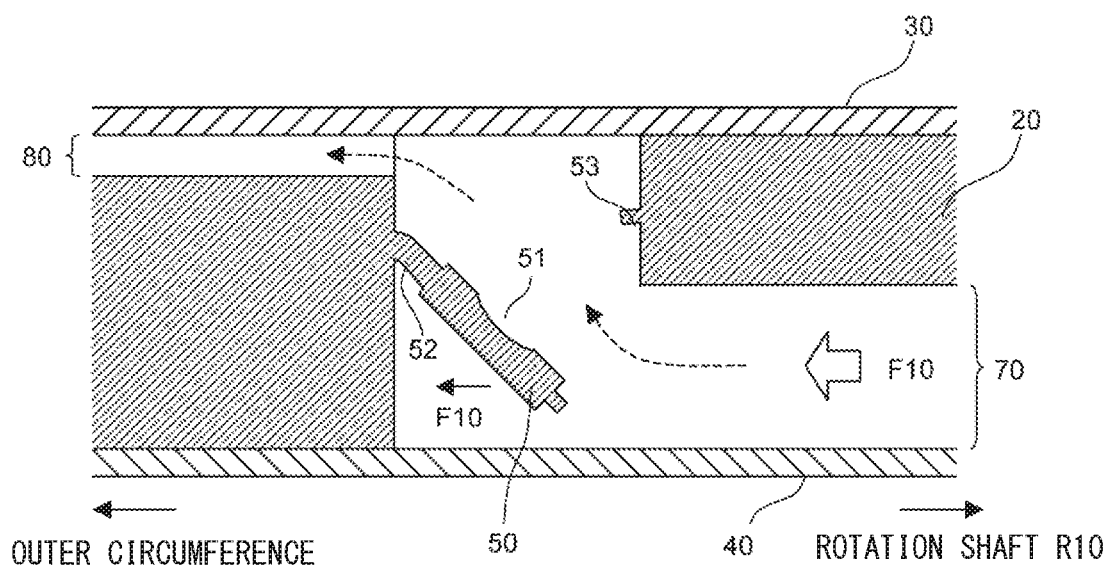

EMBODIMENT 4

FIG. 14A   EMBODIMENT 5
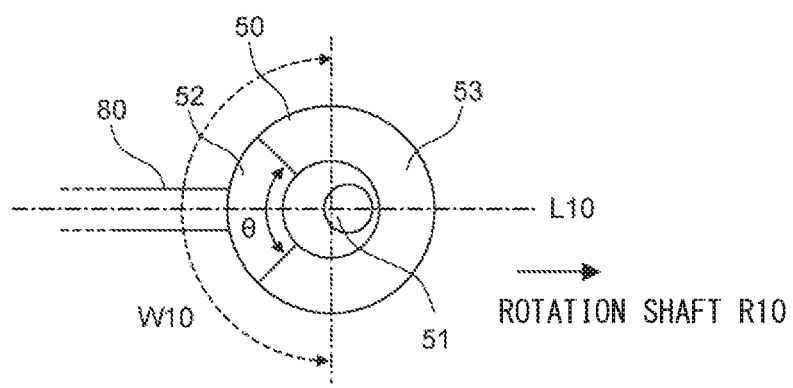
FIG. 14B
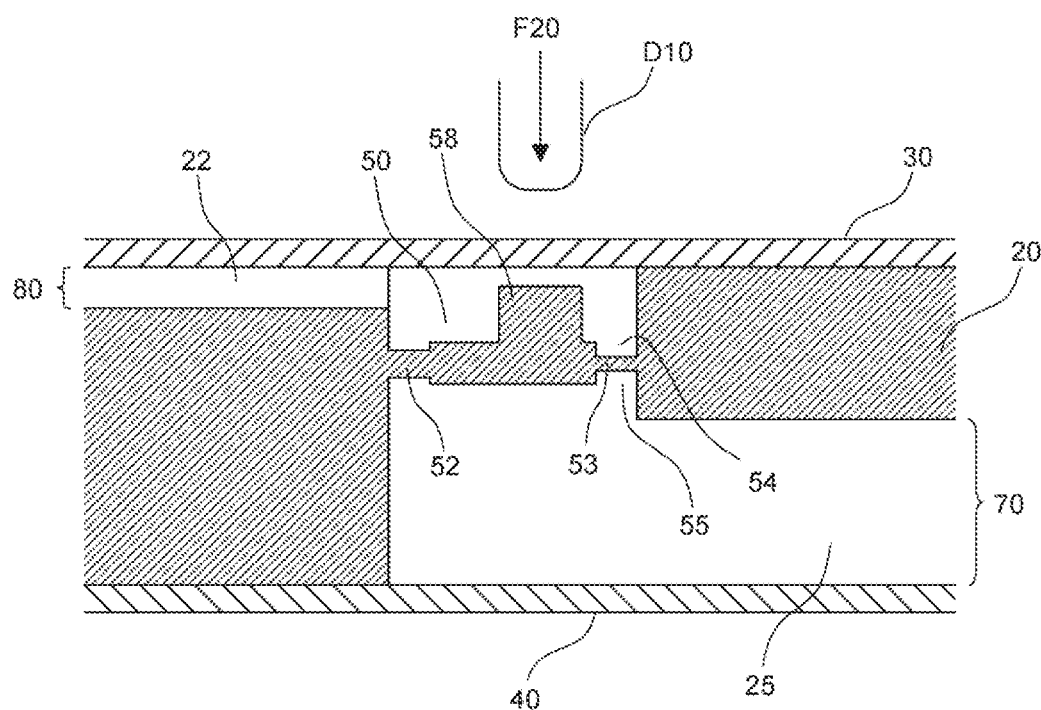

EMBODIMENT 6

FIG. 16A                                                                                         EMBODIMENT 7
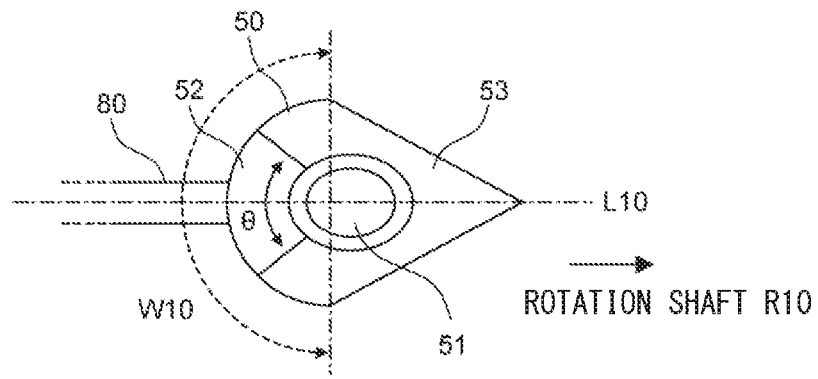
FIG. 16B
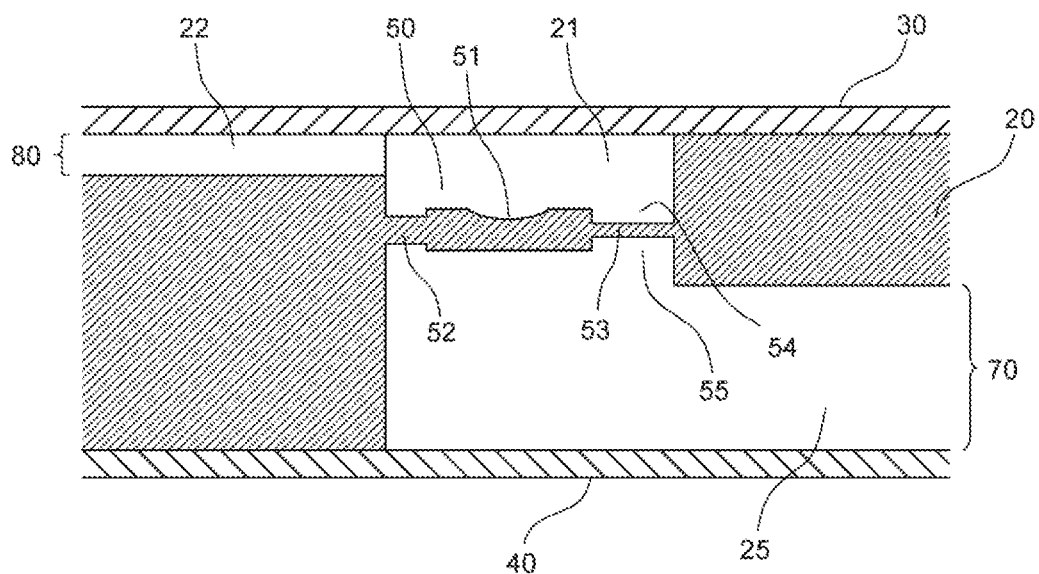
FIG. 16C                                                                                         EMBODIMENT 8
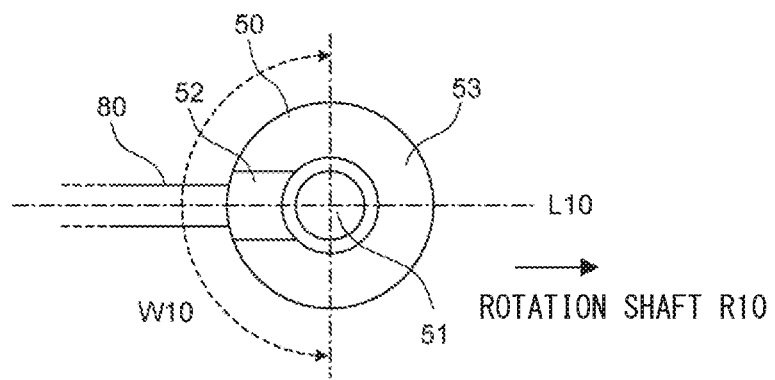

LIQUID-SEALED CARTRIDGE AND LIQUID TRANSFERRING METHOD

CROSS REFERENCE TO RELATED APPLICATIONS

This application claims priority from prior Japanese Patent Application No. 2016-211492, filed on Oct. 28, 2016, entitled "LIQUID-SEALED CARTRIDGE AND LIQUID TRANSFERRING METHOD", the entire content of which is incorporated herein by reference.

FIELD OF THE INVENTION

The present invention relates a liquid-sealed cartridge in which a liquid is stored in advance, and a liquid transferring method for transferring the liquid in the liquid-sealed cartridge.

BACKGROUND

As shown in FIG. 17, US Patent Application Publication No. 2009/074626 (hereinafter, referred to as Patent Literature 1) discloses a carrier 300 including: hollow chambers 301 and 302; a blocking element 303 for sealing a liquid in the hollow chamber 301; a removal chamber 304 via which the liquid is removed; and a channel 305 for transferring the liquid from the hollow chamber 302 to the removal chamber 304. The carrier 300 has a disk shape, and the removal chamber 304 is disposed on the center side of the carrier 300 with respect to the hollow chamber 301.

In this configuration, the blocking element 303 includes a hinge area on which the blocking element 303 is pivotable. When the blocking element 303 is pivoted downward, the liquid sealed in the hollow chamber 301 flows into the hollow chamber 302. Thereafter, the liquid moves from the hollow chamber 302 to the removal chamber 304 due to a capillary force of the channel 305. Thus, the liquid is transferred from the hollow chamber 301 to the removal chamber 304.

In the configuration of Patent Literature 1 described above, since the liquid is transferred by the capillary force of the channel 305, it is difficult to speedily transfer the liquid to the removal chamber 304.

In the configuration of Patent Literature 1, since the removal chamber 304 is located on the center side of the carrier 300 with respect to the hollow chamber 302, even if the carrier 300 is rotated, a direction in which a centrifugal force is applied is a direction from the removal chamber 304 toward the hollow chamber 302. Therefore, in the configuration of Patent Literature 1, the liquid cannot be transferred from the hollow chamber 302 to the removal chamber 304 by using the centrifugal force.

SUMMARY OF THE INVENTION

The scope of the present invention is defined solely by the appended claims, and is not affected to any degree by the statements within this summary.

A first mode of the present invention relates to a liquid-sealed cartridge (10) in which the liquid is transferred by a centrifugal force (F10) generated when the liquid-sealed cartridge (10) is rotated around a rotation shaft (R10). The liquid-sealed cartridge (10) according to the present mode includes: a liquid storage portion (70) configured to store the liquid therein; a seal (50) which has an outer peripheral portion connected to the liquid storage portion (70), and is configured to seal the inside of the liquid storage portion (70); and a flow path (80) which is connected to the liquid storage portion (70) via the seal (50), through which the liquid in the liquid storage portion (70) is transferred by the centrifugal force (F10) in a direction away from the rotation shaft (R10). When the seal (50) receives a pressing force (F20), the seal (50) is inclined in a pressing direction, with one portion (52) of the outer peripheral portion thereof remaining connected to the liquid storage portion (70), and another portion (53) of the outer peripheral portion being separated from the liquid storage portion (70).

A second mode of the present invention relates to a liquid transferring method using a liquid-sealed cartridge (200, 10) including a liquid storage portion (231, 70) configured to store a liquid therein, and a seal (232, 50) configured to seal the liquid storage portion (231, 70). The liquid transferring method according to the present mode includes: pressing the seal (232, 50) to incline the seal (232, 50) in a pressing direction, with a portion (52) of the seal (232, 50) remaining connected to the liquid storage portion (231, 70), thereby to unseal the liquid storage portion (231, 70); and rotating the liquid-sealed cartridge (200, 10) to transfer the liquid from the unsealed liquid storage portion (231, 70).

BRIEF DESCRIPTION OF THE DRAWINGS

FIG. 1A is a plan view schematically showing the structure of a liquid-sealed cartridge according to Embodiment 1;

FIG. 1B is a schematic diagram showing the structure of a flow path near a liquid storage portion of the liquid-sealed cartridge according to Embodiment 1, as viewed in a circumferential direction of the liquid-sealed cartridge;

FIG. 1C is a schematic diagram showing the structure of the flow path near the liquid storage portion of the liquid-sealed cartridge according to Embodiment 1, as viewed in the circumferential direction of the liquid-sealed cartridge;

FIG. 7 is a schematic cross-sectional view of the measurement apparatus taken along a plane parallel to a YZ plane passing a rotation shaft, as viewed from the side thereof, according to the specific configuration example of Embodiment 1;

FIG. 10 is a flowchart showing, in detail, a process for transferring a reagent to a storage chamber according to the specific configuration example of Embodiment 1;

FIG. 11A is a cross-sectional view schematically showing the structures of a seal and a liquid storage portion and a process for opening the seal, according to Embodiment 2;

FIG. 11B is a cross-sectional view schematically showing the structures of the seal and the liquid storage portion and the process for opening the seal, according to Embodiment 2;

FIG. 12A is a cross-sectional view schematically showing the structures of a seal and a liquid storage portion and a process for opening the seal, according to Embodiment 3;

FIG. 12B is a cross-sectional view schematically showing the structures of the seal and the liquid storage portion and the process for opening the seal, according to Embodiment 3;

FIG. 14A is a plan view showing the structure of a seal according to Embodiment 5;

FIG. 14B is a cross-sectional view schematically showing the structures of a seal and a liquid storage portion according to Embodiment 5;

FIG. 16A is a plan view showing the structure of a seal according to Embodiment 7;

FIG. 16B is a cross-sectional view schematically showing the structures of a seal and a liquid storage portion according to Embodiment 7;

FIG. 16C is a plan view showing the structure of a seal according to Embodiment 8.

DETAILED DESCRIPTION OF THE PREFERRED EMBODIMENTS

Embodiment 1

Figure 2A:
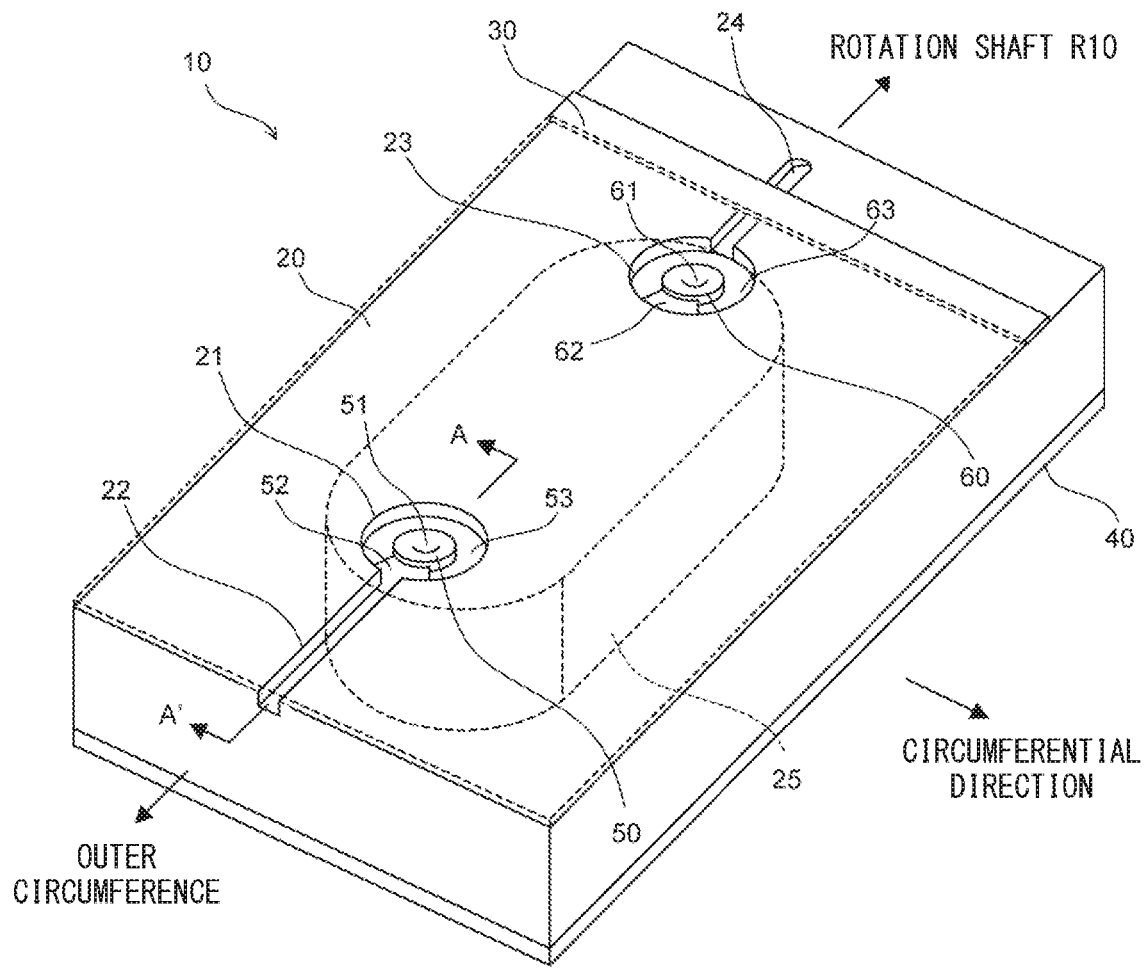
FIG. 2A is a perspective view schematically showing a constituent body obtained by cutting out a portion, near the liquid storage portion, of the liquid-sealed cartridge according to Embodiment 1.

As shown in FIG. 1A, a liquid-sealed cartridge 10 has a disk shape, and has a round opening 11 at the center thereof. The opening 11 of the liquid-sealed cartridge 10 is fitted to a rotation shaft R10 of an apparatus, whereby the liquid-sealed cartridge 10 is mounted on the apparatus so as to be rotatable around the rotation shaft R10. The shape of the liquid-sealed cartridge 10 is not limited to a disk shape, and may be a square plate shape, for example. The liquid-sealed cartridge 10 may have any shape as long as it can be mounted on the apparatus rotatably around the rotation shaft R10. The liquid-sealed cartridge 10 may have any structure as long as a liquid stored in a liquid storage portion 70 is transferred in a direction toward the outer circumference by a centrifugal force F10 generated by the rotation of the cartridge 10 around the rotation shaft R10.

The liquid-sealed cartridge 10 includes seals 50 and 60, the liquid storage portion 70, and flow paths 80 and 90.

The seals 50 and 60 seal the liquid storage portion 70. The liquid storage portion 70 stores a liquid therein. An injection hole 71 and an air hole 72 are connected to the liquid storage portion 70. The liquid is injected from the injection hole 71 into the liquid storage portion 70. Air that has stayed in the liquid storage portion 70 before injection of the liquid is discharged from the air hole 72 as the liquid is injected into the liquid storage portion 70. When the injection of the liquid is completed, the injection hole 71 and the air hole 72 are closed by seal members or the like. The flow path 80 is a flow path for transferring the liquid inside the liquid storage portion 70 in a direction away from the rotation shaft R10 by the centrifugal force F10. The flow path 90 is a flow path for introducing air into the liquid storage portion 70 when the liquid is transferred. The flow path 90 is connected to an air hole 91 for introducing air.

As shown in FIGS. 1B and 1C, the flow paths 80 and 90 are connected to the seals 50 and 60 at the opposite side from the liquid storage portion 70. The flow paths 80 and 90 are connected to the liquid storage portion 70 via the seals 50 and 60, respectively. When the liquid stored in the liquid storage portion 70 is transferred, pressing forces F20 and F30 are applied to the seals 50 and 60, respectively, as shown in FIG. 1B. Each of the seals 50 and 60 has a structure in which, when receiving the pressing force F20, F30, a portion of an outer periphery thereof remains connected to the liquid storage portion 70 while the other portion thereof is separated from the liquid storage portion 70 and inclined in the pressing direction. Therefore, as shown in FIG. 1C, the seals 50 and 60 are inclined in the pressing direction when receiving the pressing forces F20 and F30, respectively. Thus, sealing by the seals 50 and 60 is released, and openings are formed at the positions of the seals 50 and 60.

Thereafter, the liquid-sealed cartridge 10 is rotated around the rotation shaft R10, and the centrifugal force F10 is applied to the liquid in the liquid storage portion 70. Thereby, as shown in FIG. 1C, the liquid in the liquid storage portion 70 is transferred in the direction toward the outer circumference through the flow path 80, while air is introduced from the flow path 90 into the liquid storage portion 70.

Figure 2B:
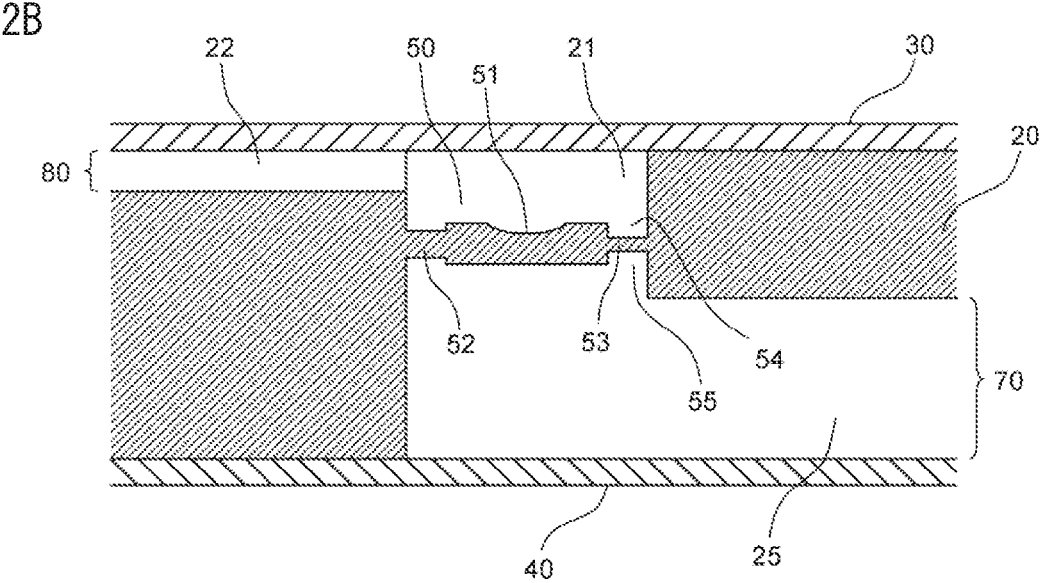
FIG. 2B is a cross-sectional view taken along a line A-A' in FIG. 2A.

As shown in FIGS. 2A and 2B, the liquid-sealed cartridge 10 may be composed of a base plate 20, and two films 30 and 40. FIG. 2A shows a constituent body obtained by cutting out a portion, near one liquid storage portion 70, of the liquid-sealed cartridge 10. Since FIG. 2A shows the structure at the upper surface of the base plate 20, for convenience, a portion, on the rotation shaft R10 side, of the film 30 attached to the upper surface of the base plate 20 is shown by a solid line while the other portion of the film 30 is shown by a broken line.

The base plate 20 is formed from a resin material such as PET (polyethylene terephthalate). The base plate 20 may be formed from transparent PMMA (polymethyl methacrylate), PC (polycarbonate), or COP (cycloolefin polymer). The base plate 20 forms a base of the liquid-sealed cartridge 10. The shape of the base plate 20 as a whole is a disk shape substantially the same as the shape of the liquid-sealed cartridge 10. At the upper surface of the base plate 20, a recess 21 which is round in a planar view and a groove 22 extending from the recess 21 toward the outer circumference, are formed. In addition, at the upper surface of the base plate 20, a recess 23 which is round in a planar view and a groove 24 extending from the recess 23 toward the rotation shaft R10, are formed on the rotation shaft R10 side relative to the recess 21. The diameters of the recesses 21 and 23 are about 2.0 mm, for example.

The groove 22 may not necessarily extend in the direction toward the outer circumference, i.e., the radial direction of the liquid-sealed cartridge 10, and may extend so as to incline in the circumferential direction of the liquid-sealed cartridge 10 with respect to the direction toward the outer circumference. The groove 24 may not necessarily extend in the direction toward the rotation shaft R10, and may incline in the circumferential direction with respect to the direction toward the rotation shaft R10. The grooves 22 and 24 may not necessarily extend linearly.

The film 30 is an elastic covering body that covers the upper surface of the base plate 20 in an elastically deformable manner. The film 30 is formed from an elastically deformable material such as elastomer or rubber. The film 30 is attached to the upper surface of the base plate 20 so as to substantially cover an area from a position slightly on the outer circumference side relative to an end of the groove 24 on the rotation shaft R10 side, to an end of the base plate 20 on the outer circumference side.

At a lower surface of the base plate 20, a recess 25 having a track shape in a planar view is formed. The recess 25 is disposed such that the recesses 21 and 23 are opposed to a position of the recess 25 on the outer circumference side and a position of the recess 25 on the rotation shaft R10 side, respectively. The seals 50 and 60 are formed in the recesses 21 and 23, respectively. The seals 50 and 60 seal the insides of the recesses 21 and 23 from the upper surface side.

The film 40 is a covering body that covers the lower surface of the base plate 20. In contrast to the film 30, the film 40 is formed from a material that is not elastically deformable, such as resin.

When the film 40 is attached to the lower surface of the base plate 20, the recess 25 is covered with the film 40. Thus, the liquid storage portion 70 is formed. The liquid storage portion 70 is a space surrounded by the recess 25 and the film 40. A liquid is injected from the injection hole 71 (refer to FIG. 1A) into the liquid storage portion 70. The inside of the liquid storage portion 70 is sealed by the seals 50 and 60 from the upper surface side.

Since the film 30 is attached to the upper surface of the base plate 20, the recesses 21 and 23 and the grooves 22 and 24 are covered with the film 30. The groove 22 being covered with the film 30 forms the flow path 80. The flow path 80 is a path for transferring the liquid in the liquid storage portion 70 toward the outer circumference side by a centrifugal force after the seals 50 and 60 are opened to unseal the liquid storage portion 70. The groove 24 being covered with the film 30 forms the flow path 90. The flow path 90 is a path for introducing air into the liquid storage portion 70 when the liquid in the liquid storage portion 70 is transferred toward the outer circumference side by the centrifugal force after the seals 50 and 60 are opened to unseal the liquid storage portion 70. An end portion of the groove 24 on the rotation shaft R10 side, which is not covered with the film 30, forms the air hole 91 shown in FIG. 1A. Air is introduced from the air hole 91 through the flow path 90 into the liquid storage portion 70.

As shown in FIGS. 2A and 2B, an outer peripheral portion of the seal 50 is connected to the liquid storage portion 70. The seal 50 is formed integrally with the liquid storage portion 70, and has a plate shape. Since the seal 50 is formed integrally with the liquid storage portion 70, the seal 50 can be easily formed.

A round recess 51 protruding downward in an arc shape is formed at a substantially center position of the upper surface of the seal 50. The diameter of the recess 51 is about 1 mm, for example. The recess 51 functions as a position defining member for defining a position at which a pressing force is applied to the seal 50. The recess 51 may not necessarily be formed at the upper surface of the seal 50, and the position of the recess 51 may be flat. The recess 51 may be disposed at a position shifted from the center position of the seal 50, e.g., a position shifted from the center position of the seal 50 toward the rotation shaft R10 side.

The outer peripheral portion of the seal 50, which is connected to the liquid storage portion 70, includes one portion forming a connecting portion 52 and the other portion forming a separation portion 53, and the thickness of the connecting portion 52 is set to be greater than the thickness of the separation portion 53. For example, the thickness of the connecting portion 52 is preferably not less than 0.15 mm, and the thickness of the separation portion 53 is preferably not greater than 0.1 mm. In this embodiment, recessed grooves 54 and 55 are formed at the upper and lower surfaces of the outer peripheral portion of the seal 50, respectively, and the thickness of the connecting portion 52 is made greater than the thickness of the separation portion 53 by changing the depths of the recessed grooves 54 and 55. The recessed grooves may not necessarily be formed on the upper and lower surfaces of the outer peripheral portion, respectively. For example, the thickness of the connecting portion 52 and the thickness of the separation portion 53 may be adjusted with a recessed groove 55 being formed only on the lower surface or the upper surface of the outer peripheral portion of the seal 50.

The connecting portion 52 is disposed at a position more distant from the rotation shaft R10 than the center of the seal 50. A straight line connecting the center of the seal 50 and the center of the connecting portion 52 in the circumferential direction is along one diameter of the liquid-sealed cartridge 10. That is, by the straight line connecting the center of the seal 50 and the center of the liquid-sealed cartridge 10, the connecting portion 52 is equally divided in the circumferential direction of the liquid-sealed cartridge 10.

The seal 60 is formed similarly to the seal 50. The seal 60 also includes a recess 61 which functions as a position defining portion, a thick connecting portion 62, and a thin separation portion 63. The connecting portion 62 is disposed at a position more distant from the rotation shaft R10 than the center of the seal 60. A straight line connecting the center of the seal 60 and the center of the connecting portion 62 in the circumferential direction is along one diameter of the liquid-sealed cartridge 10.

Figure 3A:
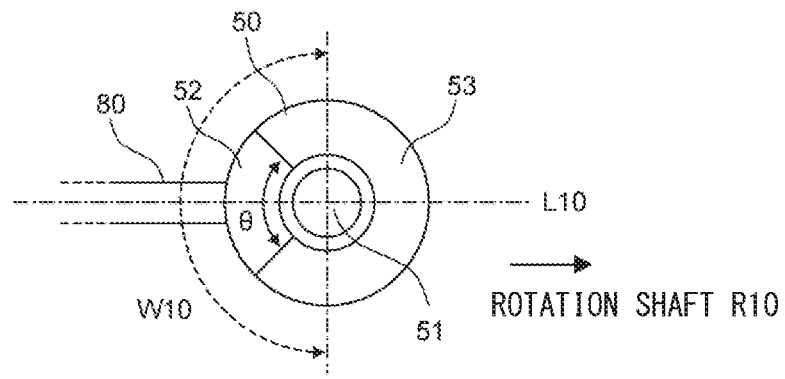
FIG. 3A is a plan view showing the structure of a seal according to Embodiment 1.

As shown in FIG. 3A, the connecting portion 52 of the seal 50 has a sector shape of an angle θ. As described above, the connecting portion 52 is disposed so as to be equally divided by one diameter L10 of the liquid-sealed cartridge 10. The connecting portion 52 preferably occupies an area not less than $1/12$ and not greater than $5/12$ of the outer peripheral portion connected to the liquid storage portion 70. Therefore, the angle θ is preferably set to be not less than 30° and not greater than 150°. Thereby, the seal 50 can be smoothly inclined by applying the pressing force F20 to the seal 50. The angle θ is preferably 60° to 120°, and more preferably 90° to 120°.

Figure 3B:
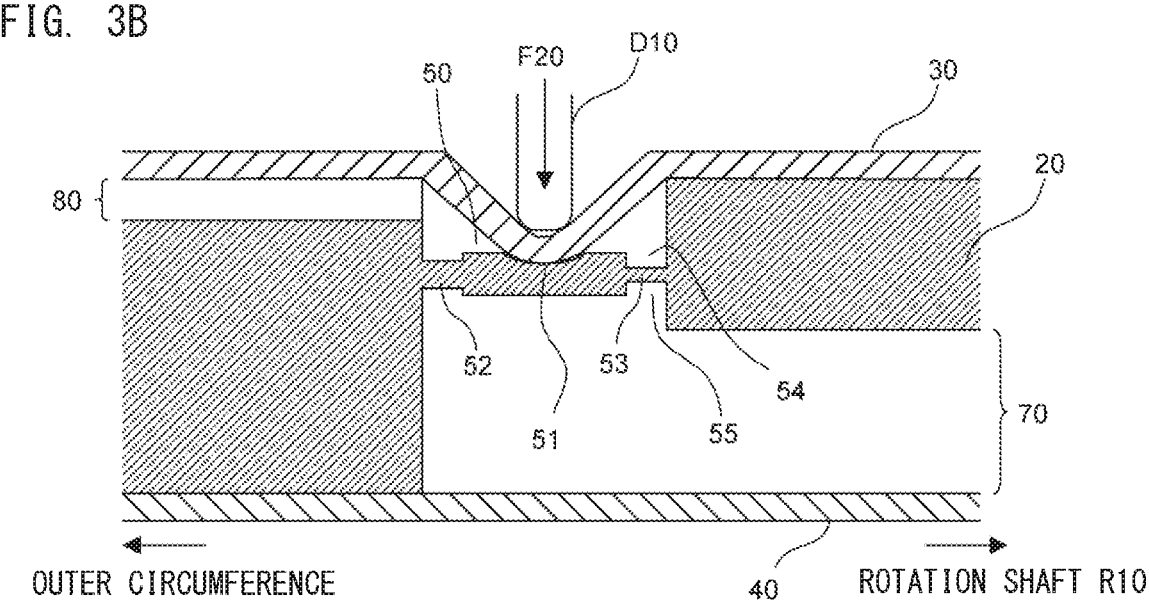
FIG. 3B is a cross-sectional view schematically showing a process for opening the seal according to Embodiment 1.

In order to open the seal 50, a rod-shaped pressing member D10 is moved downward from just above the seal 50 as shown in FIG. 3B. Thereby, the film 30 is elastically deformed downward, and the upper surface of the seal 50 is pressed by the pressing member D10. Even if the pressing position of the pressing member D10 slightly deviates from the recess 51, the pressing member D10 is led into the recess 51. Therefore, the pressing force F20 can be appropriately applied to the seal 50 at a predetermined position.

Figure 3C:
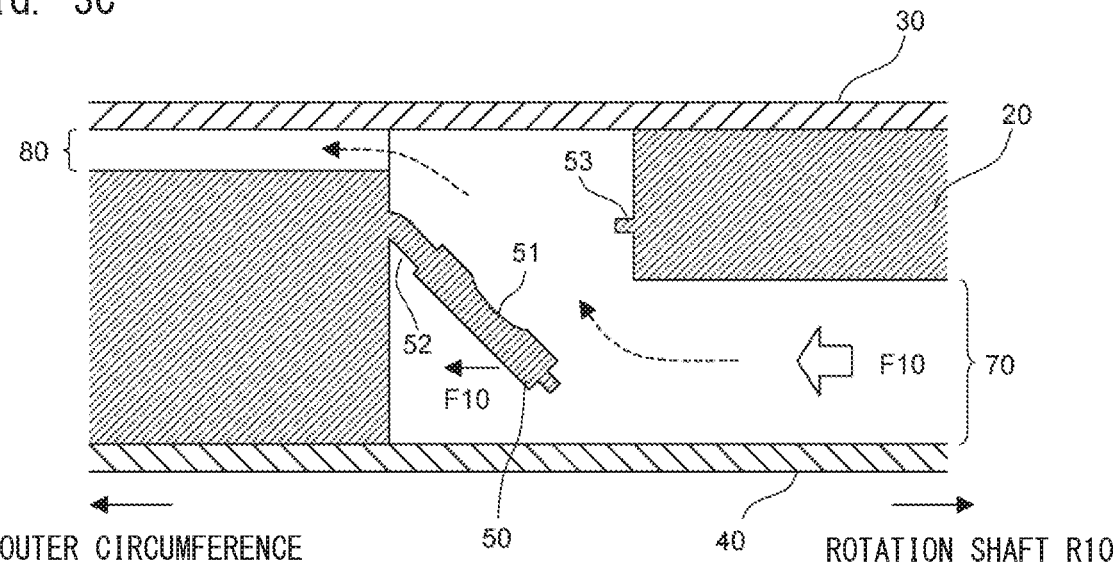
FIG. 3C is a cross-sectional view schematically showing the process for opening the seal according to Embodiment 1.

When the pressing force F20 is applied as described above, the separation portion 53 having the smaller thickness, of the outer peripheral portion of the seal 50, is broken and separated from the liquid storage portion 70, while the connecting portion 52 having the greater thickness, of the outer peripheral portion, remains connected. Thereby, as shown in FIG. 3C, the seal 50 can be inclined in the pressing direction with the connecting portion 52 remaining connected to the liquid storage portion 70. After the seal 50 is opened, the pressing member D10 is retracted upward. Thus, the film 30, which has been elastically deformed downward, is restored to the original state.

After the liquid storage portion 70 and the flow path 80 are communicated with each other as described above, the liquid-sealed cartridge 10 is rotated and the centrifugal force F10 is generated, whereby the liquid stored in the liquid storage portion 70 is transferred through the flow path 80 by the centrifugal force F10. Thus, the liquid in the liquid storage portion 70 can be speedily transferred. Since the seal 50 is connected to the liquid storage portion 70 at the connecting portion 52, even when the liquid is transferred at a high speed by the centrifugal force F10, the seal 50 is not transferred due to the flow of the liquid. Therefore, the flow path 80 or the like on the downstream side is prevented from being clogged with the seal 50, whereby transfer of the liquid can be smoothly performed. According to the liquid-sealed cartridge 10 of Embodiment 1, the sealed liquid can be smoothly and speedily transferred by the centrifugal force F10.

As shown in FIGS. 3A to 3C, the position of the connecting portion 52 of the seal 50 is set such that the centrifugal force F10 is applied in a direction in which the seal 50, which has been inclined by the pressing force F20, is further inclined. Specifically, the connecting portion 52 is provided at a position distant from the rotation shaft R10 relative to the separation portion 53. Therefore, when the liquid-sealed cartridge 10 is rotated to transfer the liquid, since the centrifugal force F10 is applied to the seal 50 in the direction in which the seal 50 is further inclined, the seal 50 is inhibited from moving in the direction in which the seal 50 is abruptly closed during liquid transfer. Thus, the sealing-released state is appropriately maintained during liquid transfer. Accordingly, transfer of the liquid to the flow path 80 can be reliably performed.

The position of the connecting portion 52 is not limited to the position shown in FIG. 3A. For example, the position of the connecting portion 52 may be shifted in the circumferential direction of the seal 50 from the position shown in FIG. 3A. However, in order to prevent the seal 50 from being abruptly closed during liquid transfer, the position of the connecting portion 52 of the seal 50 is preferably set such that the centrifugal force F10 is applied to the seal 50 in the direction in which the seal 50 inclined by the pressing force F20 is further inclined. In the structure shown in FIG. 3A, the position of the connecting portion 52 is set such that the center position of the connecting portion 52 in the circumferential direction is located within a range W10 of the seal 50 on the opposite side from the rotation shaft R10, whereby the centrifugal force F10 can be applied to the seal 50 in the direction in which the seal 50 inclined by the pressing force F20 is further inclined.

As shown in FIGS. 3B and 3C, the seal 50 is provided on the upper surface of the liquid storage portion 70, and the flow path 80 is disposed at the upper side of the liquid storage portion 70. Therefore, as shown in FIG. 3B, the liquid flowing along the inclined seal 50 can be smoothly guided to the flow path 80. Accordingly, liquid transfer by the centrifugal force F10 can be efficiently performed.

As shown in FIG. 3B, the flow path 80 is connected to the seal 50 via a gap between the seal 50 and the elastically deformable film 30, and the seal 50 is pressed via the film 30. Thus, the seal 50 can be smoothly pressed via the film 30, whereby sealing by the seal 50 can be smoothly released.

As shown in FIG. 2A, the liquid storage portion 70 is provided with the two seals 50 and 60. Therefore, air can be introduced into the liquid storage portion 70 during liquid transfer by opening the seal 60, whereby the liquid in the liquid storage portion 70 can be smoothly transferred. Since the seal 60 is also opened so as to be inclined with a portion thereof remaining connected to the liquid storage portion 70, this seal 60 is inhibited from being transferred and causing clogging in the downstream side flow path or the like when the liquid is transferred.

As shown in FIGS. 3A and 3B, the seal 50 has the recessed grooves 54 and 55 formed at the outer peripheral portion thereof, and the thickness of the connecting portion 52 is set to be greater than the thickness of the separation portion 53 by changing the depths of the recessed grooves 54 and 55. Since the recessed grooves 54 and 55 are formed also in the connecting portion 52 which remains connected to the liquid storage portion 70 after sealing is released, the seal 50 is flexibly supported at the connecting portion 52 after the sealing release, and the seal 50 is less likely to be restored to the position before the sealing release. Thus, the seal 50 can be stably maintained in the released state without the necessity of providing a mechanism for compulsorily maintaining the seal 50 in the released state.

When the liquid is transferred, the liquid-sealed cartridge 10 is rotated at a rotation speed of 100 to 10000 rpm, for example. Since the liquid-sealed cartridge 10 is rotated at the rotation speed, the liquid in the liquid storage portion 70 can be smoothly transferred by the centrifugal force F10.

The liquid stored in the liquid storage portion 70 is, for example, a reagent used for measurement of a specimen. In this case, since the reagent can be smoothly and speedily transferred, measurement on the apparatus side can be appropriately and speedily advanced.

Figure 4A:
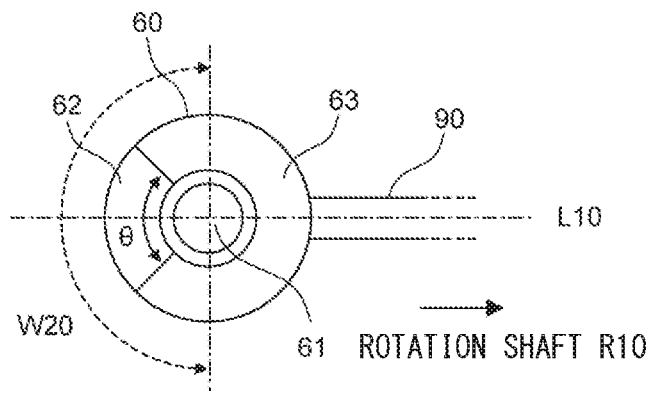
FIG. 4A is a plan view showing the structure of a seal for air introduction according to Embodiment 1.
Figure 4B:
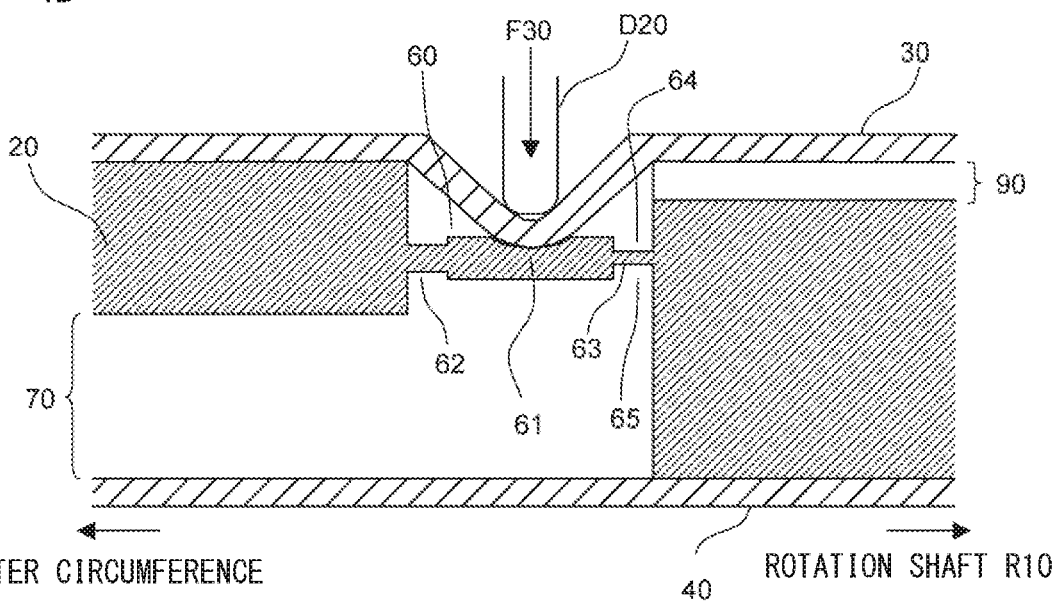
FIG. 4B is a cross-sectional view schematically showing a process for opening the seal for air introduction according to Embodiment 1.
Figure 4C:
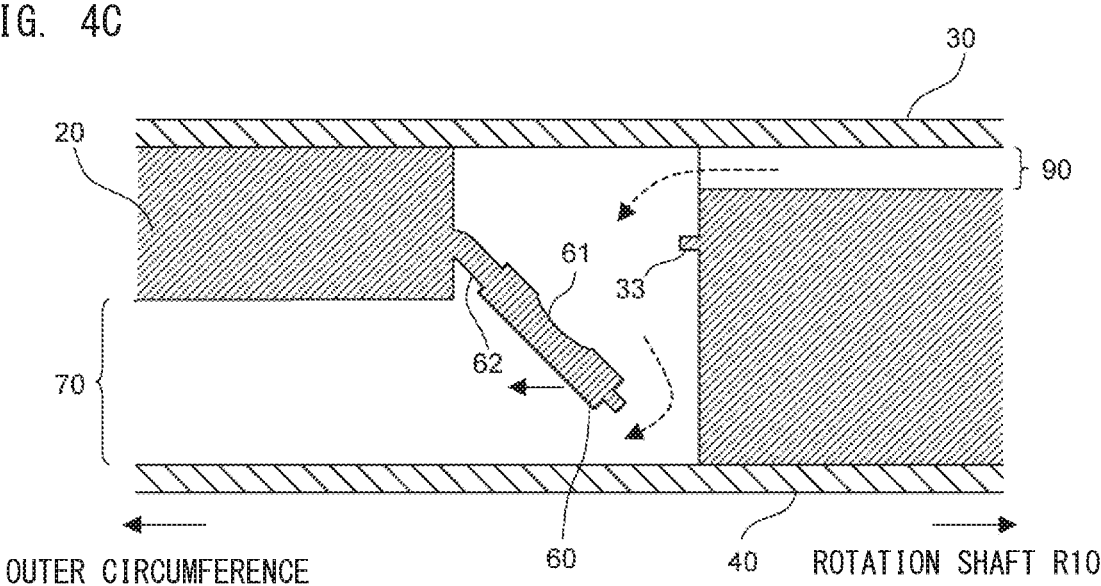
FIG. 4C is a cross-sectional view schematically showing the process for opening the seal for air introduction according to Embodiment 1.

As shown in FIGS. 4A to 4C, the seal 60 on the rotation shaft R10 side has the same structure as that of the seal 50 shown in FIGS. 3A to 3C, except the connection position of the flow path 90. A connecting portion 62 and a separation portion 63 are formed by changing the depths of recessed grooves 64 and 65. The connecting portion 62 has a sector shape of an angle θ. The connecting portion 62 is disposed so as to be equally divided by one diameter L10 of the liquid-sealed cartridge 10. The connecting portion 62 preferably occupies an area not less than 1/12 and not greater than 5/12 of the outer peripheral portion connected to the liquid storage portion 70. The angle θ is preferably set to be not less than 30° and not greater than 150°.

The position of the connecting portion 62 is not necessarily limited to the position shown in FIG. 4A. For example, the position of the connecting portion 62 may be shifted in the circumferential direction of the seal 60 from the position shown in FIG. 4A. However, in order to prevent the seal 60 from being abruptly closed during liquid transfer, the position of the connecting portion 62 of the seal 60 is preferably set such that the centrifugal force F10 is applied to the seal 60 in a direction in which the seal 60 inclined by the pressing force F30 is further inclined. In the structure shown in FIG. 4A, the position of the connecting portion 62 is set such that the center position of the connecting portion 62 in the circumferential direction is located within a range W20 of the seal 60 on the opposite side from the rotation shaft R10, whereby the centrifugal force F10 can be applied to the seal 60 in the direction in which the seal 60 inclined by the pressing force F30 is further inclined.

As shown in FIG. 4B, the seal 60 is pressed by a pressing member D20 via the film 30. Thereby, the thin separation portion 63 is broken while the thick connecting portion 62 remains connected. Thereby, as shown in FIG. 4C, the seal 60 is inclined and opened. After the seal 50 is opened, the pressing member D20 is retracted upward. Thus, the film 30, which has been elastically deformed downward, is restored to the original state. As shown in FIG. 4C, when the liquid is transferred, air is introduced from the flow path 90 into the liquid storage portion 70. Thus, the liquid in the liquid storage portion 70 is smoothly transferred in the direction toward the outer circumference.

As shown in FIGS. 3A to 3C and FIGS. 4A to 4C, the direction in which the seal 50, 60 is inclined can be defined by providing the thick connecting portion 52, 62. In addition, since the outer peripheral portion of the seal 50, 60 is gradually broken from the thinner portion by the pressing force F20, F30, the pressing force F20, F30 required for opening the seal 50, 60 can be reduced. Therefore, a driving mechanism for the pressing member D10, D20 can be downsized, thereby realizing downsizing of the apparatus.

<Specific Configuration Example>

Hereinafter, a specific configuration example of the liquid-sealed cartridge 10 when being used for measurement of a specimen will be described together with the structure of a measurement apparatus.

Figure 5A:
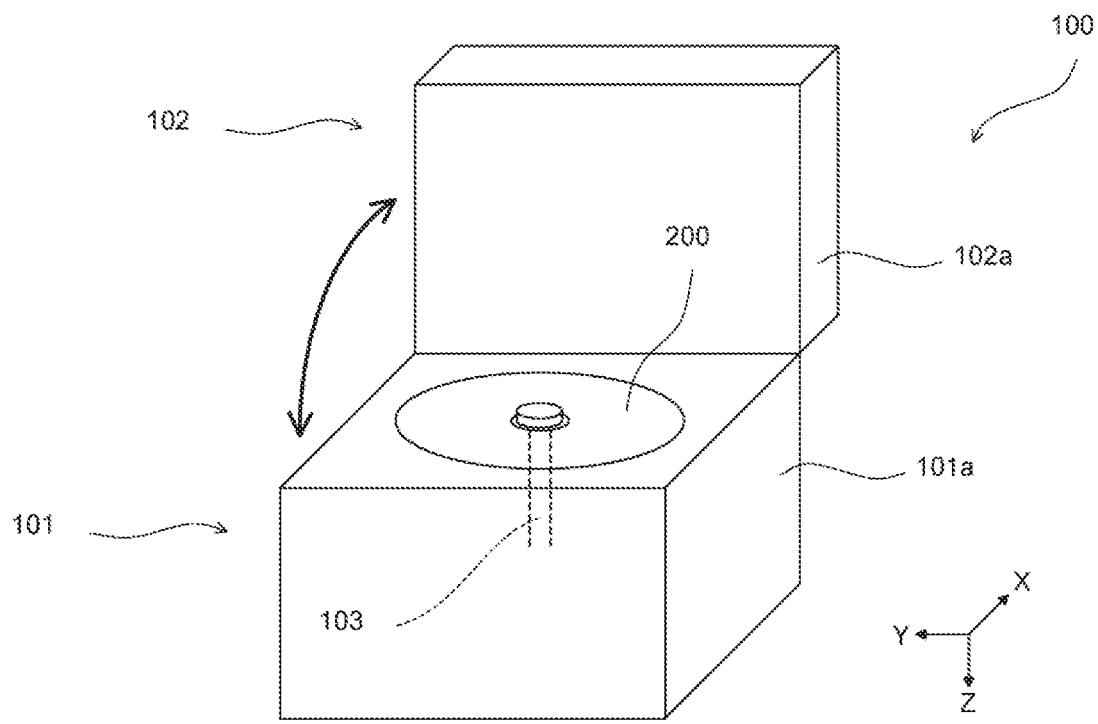
FIG. 5A is a schematic diagram showing the structure of a measurement apparatus according to a specific configuration example of Embodiment 1.

With reference to FIG. 5A, a measurement apparatus 100 is an immune analyzer that measures a specimen by using a liquid-sealed cartridge 200. The specimen is a whole blood specimen collected from a subject. The measurement apparatus 100 detects a test substance in the specimen by utilizing antigen-antibody reaction, and analyzes the test substance on the basis of the detection results.

The measurement apparatus 100 includes a body 101 and a lid 102. The body 101, except a portion thereof opposed to the lid 102, is covered with a casing 101a. The lid 102, except a portion thereof opposed to the body 101, is covered with a casing 102a. The body 101 supports the lid 102 so that the lid 102 is openable/closable with respect to the body 101.

When the liquid-sealed cartridge 200 is mounted or demounted, the lid 102 is opened as shown in FIG. 5A. The liquid-sealed cartridge 200 is mounted on an upper portion of the body 101. The body 101 includes a rotation shaft 103 extending in parallel to the Z-axis direction. The rotation shaft 103 corresponds to the rotation shaft R10 shown in FIG. 1A. The measurement apparatus 100 rotates the mounted liquid-sealed cartridge 200 around the rotation shaft 103. The internal structure of the measurement apparatus 100 will be later described with reference to FIGS. 6 to 8.

Figure 5B:
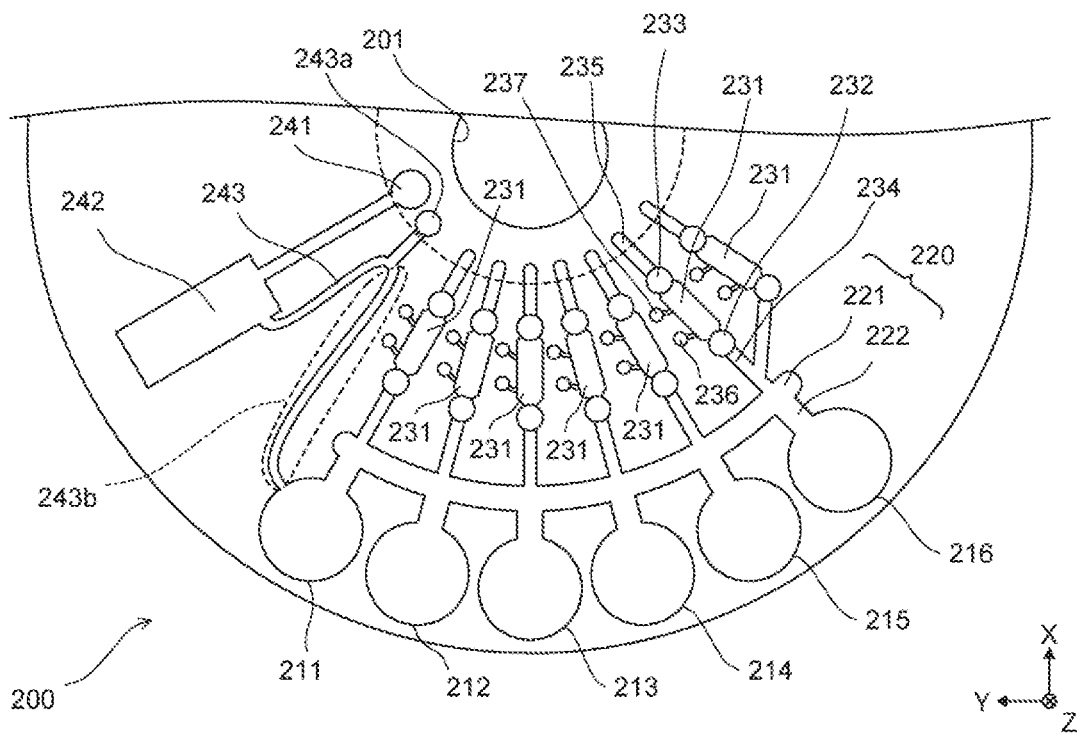
FIG. 5B is a schematic diagram showing the structure of a liquid-sealed cartridge according to the specific configuration example of Embodiment 1.

As shown in FIG. 5B, the liquid-sealed cartridge 200 is a disk-shaped cartridge having a predetermined thickness. As in the structure shown in FIGS. 2A and 2B, the liquid-sealed cartridge 200 is formed by bonding films to the upper and lower surfaces of a base plate. In FIG. 5B, an arc-shaped broken line outside an opening 201 indicates an inner circumference side boundary of the film bonded to the upper surface of the base plate. The base plate and the two films are formed from a translucent material.

The liquid-sealed cartridge 200 includes a plurality of structures each being composed of a liquid storage portion 231, seals 232 and 233, flow paths 234 and 235, an injection hole 236, and an air hole 237. The liquid storage portion 231, the seals 232 and 233, the flow paths 234 and 235, the injection hole 236, and the air hole 237 correspond to the liquid storage portion 70, the seals 50 and 60, the flow paths 80 and 90, the injection hole 71, and the air hole 72 which are shown in FIG. 1A, respectively. The structures and the formation methods of the liquid storage portion 231, the seals 232 and 233, the flow paths 234 and 235, the injection hole 236, and the air hole 237 provided in the liquid-sealed cartridge 200 are identical to those of the liquid storage portion 70, the seals 50 and 60, the flow paths 80 and 90, the injection hole 71, and the air hole 72 shown in FIGS. 1A to 4C.

Reagents used for measurement are injected into the seven liquid storage portions 231 arranged in the circumferential direction, respectively. The reagents to be stored include not only reagents for generating antigen-antibody reactions but also a washing liquid. As in the case of FIG. 1A, the reagent to be stored in each liquid storage portion 231 is injected through the injection hole 236. At this time, air stored in the liquid storage portion 231 is discharged from the air hole 237 due to the injection of the liquid. When storage of the liquid is completed, the injection hole 236 and the air hole 237 are closed by seal members or the like.

The liquid-sealed cartridge 200 further includes an opening 201, six chambers 211 to 216 arranged in the circumferential direction, a channel 220, a specimen injection hole 241, a separator 242, and a channel 243. The opening 201 penetrates the liquid-sealed cartridge 200 at the center of the liquid-sealed cartridge 200. The opening 201 corresponds to the opening 11 shown in FIG. 1A. The chambers 211 to 216, the channel 220, the separator 242, and the channel 243 are formed by closing recesses or grooves formed in the base plate, with the films bonded to the upper and lower surfaces of the base plate, like the liquid storage portions 231 and the flow paths 234 and 235.

The channel 220 includes an arc-shaped region 221 extending in the circumferential direction, and six regions 222 extending in the radial direction. The region 221 is connected to the six regions 222. The six regions 222 are connected to the chambers 211 to 216, respectively. The seven liquid storage portions 231 are connected to the channel 220 via the flow paths 234. Among the seven liquid storage portions 231, the six liquid storage portions 231 on the Y-axis positive side are present on extensions of the regions 222 connected to the chambers 211 to 216, respectively. The liquid storage portion 231 on the Y-axis most negative side is connected to the flow path 234 which extends from the adjacent liquid storage portion 231 on the Y-axis position side, toward the chamber 216.

The whole blood specimen collected from the subject is injected into the separator 242 via the specimen injection hole 241. The separator 242 separates the injected blood specimen into blood cells and plasma by a centrifugal force generated by rotation of the liquid-sealed cartridge 10. The plasma separated by the separator 242 is moved to the channel 243 by capillary phenomenon. A hole 243a is provided at a radially-inward upper surface of the channel 243. The plasma, which is positioned in a region 243b in the channel 243, is moved to the chamber 211 by the centrifugal force when the liquid-sealed cartridge 200 is rotated. Thus, a predetermined amount of plasma is transferred to the chamber 211.

The plasma transferred to the chamber 211 is sequentially transferred to the chambers 212 to 216 by transferring means on the measurement apparatus 100 side. The seals 232 and 233 of the liquid storage portion 231 connected to each chamber are opened, whereby the reagent is introduced from each liquid storage portion 231 into the corresponding chamber by the centrifugal force. In each chamber, processing using the introduced reagent is performed. Measurement of the test substance is performed in the Y-axis most negative side chamber 216. Processing for measurement will be later described with reference to FIG. 9 and FIG. 10.

Next, the internal structure of the measurement apparatus 100 will be described with reference to FIG. 6 to FIG. 8.

The body 101 includes a mounting member 111, a plate member 112, a support member 113, a magnetic force applying unit 114, a detector 115, a housing 116, a motor 117, and an encoder 118.

The mounting member 111 has a shape fitting into the casing 101a. The plate member 112 is mounted at the center of an upper surface of the mounting member 111. The plate member 112 is formed from a metal having high thermal conductivity. A heater 131 described later is mounted on a lower surface of the plate member 112. The support member 113 is mounted at the center of the mounting member 111 via a mounting member 119 described later. The support member 113 is implemented by, for example, a turn table.

The magnetic force applying unit 114 is mounted on a lower surface of the mounting member 111 so as to be opposed to a lower surface of the liquid-sealed cartridge 200 mounted on the support member 113, via holes formed through the mounting member 111 and the plate member 112. The magnetic force applying unit 114 includes a magnet, and a mechanism for moving the magnet in the Z-axis direction and the radial direction of the liquid-sealed cartridge 200.

The detector 115 is mounted on the lower surface of the mounting member 111 so as to be opposed to the lower surface of the liquid-sealed cartridge 200 mounted on the support member 113, via holes formed through the mounting member 111 and the plate member 112. The detector 115 includes a photodetector. The photodetector of the detector 115 optically detects the test substance stored in the chamber 216. The photodetector of the detector 115 is implemented by, for example, a photo multiplier tube, a phototube, a photodiode, or the like.

The housing 116 is mounted to the lower surface of the mounting member 111. The housing 116 includes a lower surface 116a and housing portions 116b and 116c. A hole 116d described later is formed at the center of an upper surface of the housing 116. The hole 116d penetrates the housing 116 in the vertical direction from the upper surface to the lower surface 116a. The hole 116d allows the rotation shaft 103 to pass therethrough.

The housing portions 116b and 116c are configured as recesses protruding downward from the upper surface of the housing 116. The housing portions 116b and 116c house the magnetic force applying unit 114 and the detector 115, respectively. The motor 117 is implemented by a stepping motor. The motor 117 is mounted on the lower surface 116a of the housing 116, and rotates the rotation shaft 103 around the Z axis. The encoder 118 is mounted on a lower surface of the motor 117, and detects rotation of a drive shaft 117a of the motor 117 described later.

Figure 6:
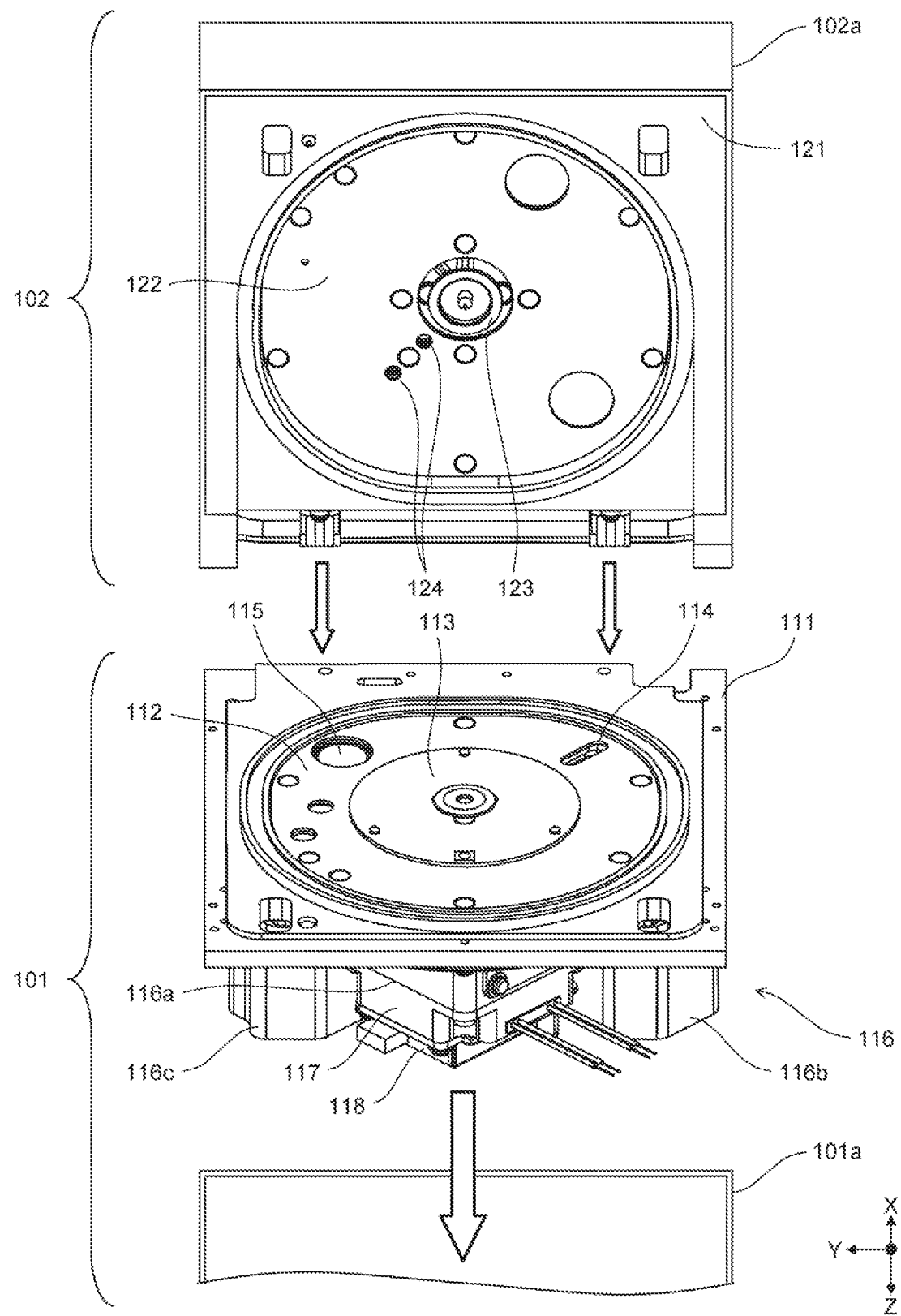
FIG. 6 shows a body as viewed from diagonally above and a lid as viewed from diagonally below, according to the specific configuration example of Embodiment 1.

An upper part of FIG. 6 shows the lid 102 as viewed from below. The lid 102 includes a mounting member 121, a plate member 122, a clamper 123, and two pressing members 124.

The mounting member 121 has a shape fitting into the casing 102a. The plate member 122 is mounted at the center of a lower surface of the mounting member 121. The plate member 122 is formed from a metal having high thermal conductivity, like the plate member 112. A heater 132 described later is mounted on an upper surface of the plate member 122. The clamper 123 is mounted at the center of the mounting member 121. The two pressing members 124 are mounted on an upper surface of the mounting member 121.

When the lid 102 is closed, the two pressing members 124 are aligned in the radial direction of the liquid-sealed cartridge 200 mounted on the support member 113. The radially inward pressing member 124 presses the seal 233 of the liquid-sealed cartridge 200 from above via the holes formed through the mounting member 121 and the plate member 122, to open the seal 233 by the pressing force. The radially outward pressing member 124 presses the seal 232 of the liquid-sealed cartridge 200 from above via the holes formed through the mounting member 121 and the plate member 122, to open the seal 232 by the pressing force.

The radially outward pressing member 124 corresponds to the pressing member D10 shown in FIG. 3B, and the radially inward pressing member 124 corresponds to the pressing member D20 shown in FIG. 4B.

When the measurement apparatus 100 is assembled, the mounting member 111 and the housing 116 which are assembled as shown in FIG. 6 are mounted in the casing 101a, thereby completing the body 101. In addition, the lid 102 assembled as shown in FIG. 6 is mounted to be openable/closable with respect to the mounting member 111 of the body 101, whereby the lid 102 is mounted to the body 101. Thus, the measurement apparatus 100 is completed.

FIG. 7 is a cross-sectional view schematically showing a cross-section of the measurement apparatus 100 when the measurement apparatus 100 is cut in a plane parallel to a YZ plane that passes the rotation shaft 103. FIG. 7 shows a state in which the liquid-sealed cartridge 200 is mounted on the measurement apparatus 100, and the lid 102 is closed. As described above, the magnetic force applying unit 114 and the detector 115 are mounted on the lower surface of the mounting member 111, and the two pressing members 124 are mounted on the upper surface of the mounting member 121. In FIG. 7, positions where these components are disposed are represented by broken lines.

As shown in FIG. 7, the drive shaft 117a of the motor 117 extends to the inside of the hole 116d. The mounting member 119 is mounted in an upper portion of the hole 116d. The mounting member 119 rotatably supports the rotation shaft 103 extending in the vertical direction. The rotation shaft 103, inside the hole 116d, is fixed to the drive shaft 117a of the motor 117 by a fixing member 117b.

The support member 113 for supporting the lower surface of the liquid-sealed cartridge 200 is fixed to an upper portion of the rotation shaft 103 via a predetermined member. When the motor 117 is driven to rotate the drive shaft 117a, a rotation driving force is transmitted to the support member 113 via the rotation shaft 103. Thereby, the liquid-sealed cartridge 200 mounted on the support member 113 rotates around the rotation shaft 103. When the liquid-sealed cartridge 200 is mounted on the support member 113 and the lid 102 is closed, the clamper 123 presses an inner circumferential portion of the upper surface of the liquid-sealed cartridge 200 so that the cartridge 200 is rotatable.

The heater 131 is mounted on the lower surface of the plate member 112, and the heater 132 is mounted on the upper surface of the plate member 122. Each of the heaters 131 and 132 has a flat heat generating surface, and is disposed such that the heat generating surface is parallel to the liquid-sealed cartridge 200. Thereby, the liquid-sealed cartridge 200 can be efficiency heated.

Figure 8:
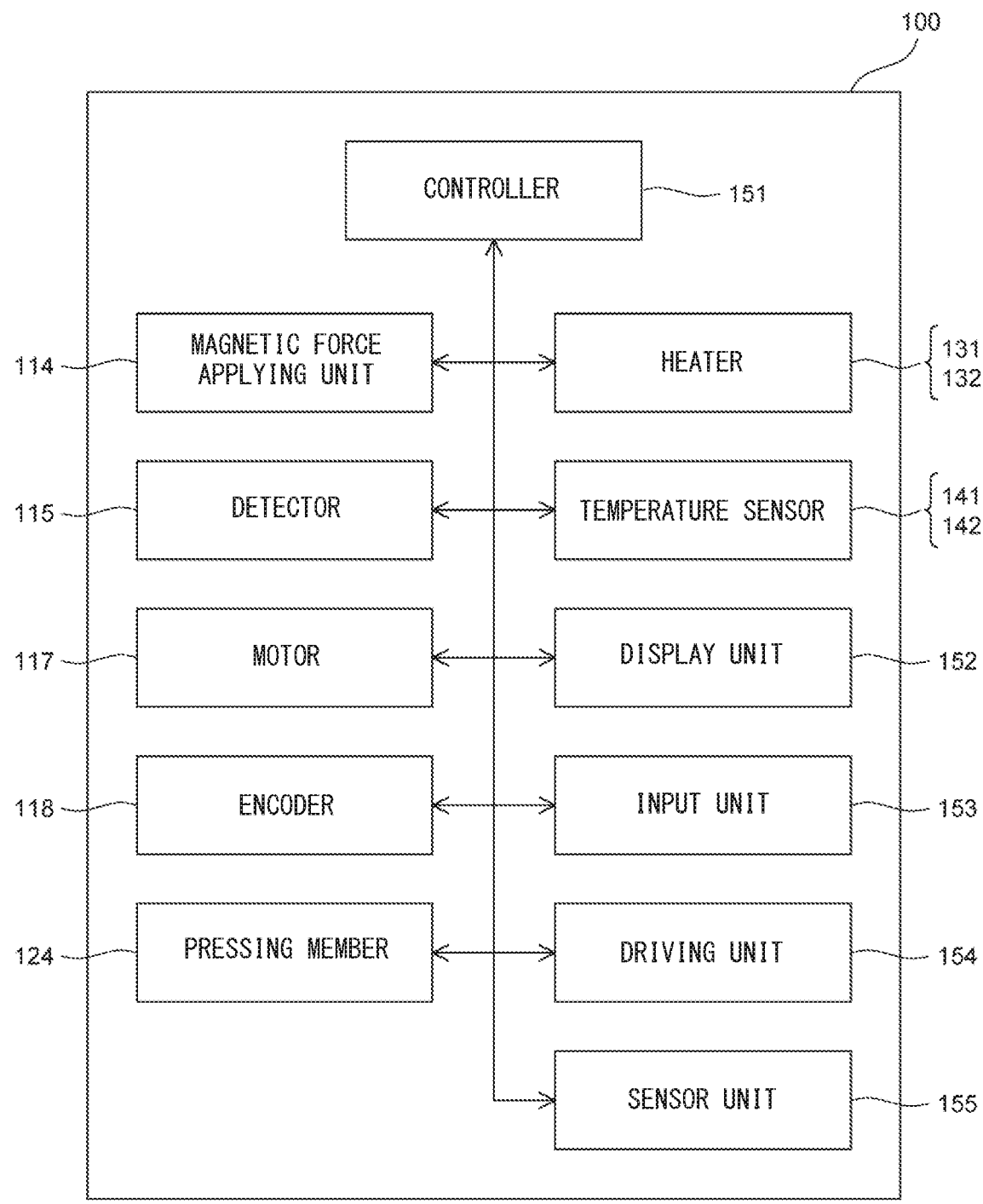
FIG. 8 is a block diagram showing the structure of the measurement apparatus according to the specific configuration example of Embodiment 1.

The plate members 112 and 122 are provided with temperature sensors 141 and 142 shown in FIG. 8, respectively. The temperature sensors 141 and 142 detect the temperatures of the plate members 112 and 122, respectively. A controller 151 described later drives the heaters 131 and 132 such that the temperature, of the plate member 112, detected by the temperature sensor 141, and the temperature, of the plate member 122, detected by the temperature sensor 142 are predetermined temperatures when measurement is performed.

The magnetic force applying unit 114, as shown by an upward dotted arrow in FIG. 7, applies a magnetic force to the liquid-sealed cartridge 200 by using a magnet. The detector 115, as shown by a downward dotted arrow in FIG. 7, receives light generated from the chamber 216 of the liquid-sealed cartridge 200. When the lid 102 is closed, passing of the light is prevented between the outside and the space in which the liquid-sealed cartridge 200 is located. Thereby, even when the light generated during the reaction process in the chamber 216 is extremely weak, since external light is prevented from entering the space in which the liquid-sealed cartridge 200 is located, the light generated by the reaction can be accurately detected by the photodetector of the detector 115.

As shown in FIG. 8, the measurement apparatus 100 includes the controller 151, a display unit 152, an input unit 153, a driving unit 154, and a sensor unit 155, in addition to the magnetic force applying unit 114, the detector 115, the motor 117, the encoder 118, the pressing member 124, the heaters 131 and 132, and the temperature sensors 141 and 142 mounted on the plate members 112 and 122 which are shown in FIG. 7.

The controller 151 includes, for example, an arithmetic processor and a storage unit. The arithmetic processor is implemented by, for example, a CPU or an MPU. The storage unit is implemented by, for example, a flash memory or a hard disk. The controller 151 receives signals from the respective components of the measurement apparatus 100, and controls the respective components of the measurement apparatus 100.

The display unit 152 and the input unit 153 are provided at, for example, a lateral face portion of the body 101 or an upper face portion of the lid 102. The display unit 152 is implemented by, for example, a liquid crystal panel. The input unit 153 is implemented by, for example, buttons or a touch panel. The driving unit 154 includes other mechanisms disposed in the measurement apparatus 100. The sensor unit 155 includes: a sensor for detecting a predetermined portion of the liquid-sealed cartridge 200 mounted on the support member 113; and other sensors disposed in the measurement apparatus 100.

Next, the operation of the measurement apparatus 100 is described with reference to FIG. 9.

First, an operator injects a specimen collected from a subject into the liquid-sealed cartridge 200 from the specimen injection hole 241, and places the liquid-sealed cartridge 200 on the support member 113. The specimen injected from the specimen injection hole 241 is stored in the separator 242. The test substance in the specimen contains an antigen, for example. An example of the antigen is hepatitis B surface antigen (HBsAg). The test substance may be one or more of an antigen, an antibody, and a protein.

Predetermined reagents are stored in the seven liquid storage portions 231 and the chamber 211 of the liquid-sealed cartridge 200 in advance. Specifically, an R1 reagent is stored in the liquid storage portion 231 positioned in the radial direction of the chamber 211. An R2 reagent is stored in the chamber 211. An R3 reagent is stored in the liquid storage portion 231 positioned in the radial direction of the chamber 212. A washing liquid is stored in the liquid storage portions 231 positioned in the radial directions of the chambers 213 to 215. An R4 reagent is stored in the liquid storage portion 231 positioned in the radial direction of the chamber 216. An R5 reagent is stored in the liquid storage portion 231 on the Y-axis negative side of the liquid storage portion 231 in which the R4 reagent is stored.

In a control described below, the controller 151 obtains a rotation position of the drive shaft 117a of the motor 117 on the basis of an output signal from the encoder 118 connected to the motor 117. The controller 151 obtains a reference position of the liquid-sealed cartridge 200 in the rotation direction by detecting, with the sensor, a predetermined portion of the rotating liquid-sealed cartridge 200. On the basis of the reference position and the output signal from the encoder 118, the controller 151 locates the respective components of the liquid-sealed cartridge 200 at predetermined positions in the rotation direction. In addition, on the basis of the outputs from the temperature sensors 141 and 142, the controller 151 controls the heaters 131 and 132 such that the temperature near the liquid-sealed cartridge 200 is kept constant.

Figure 9:
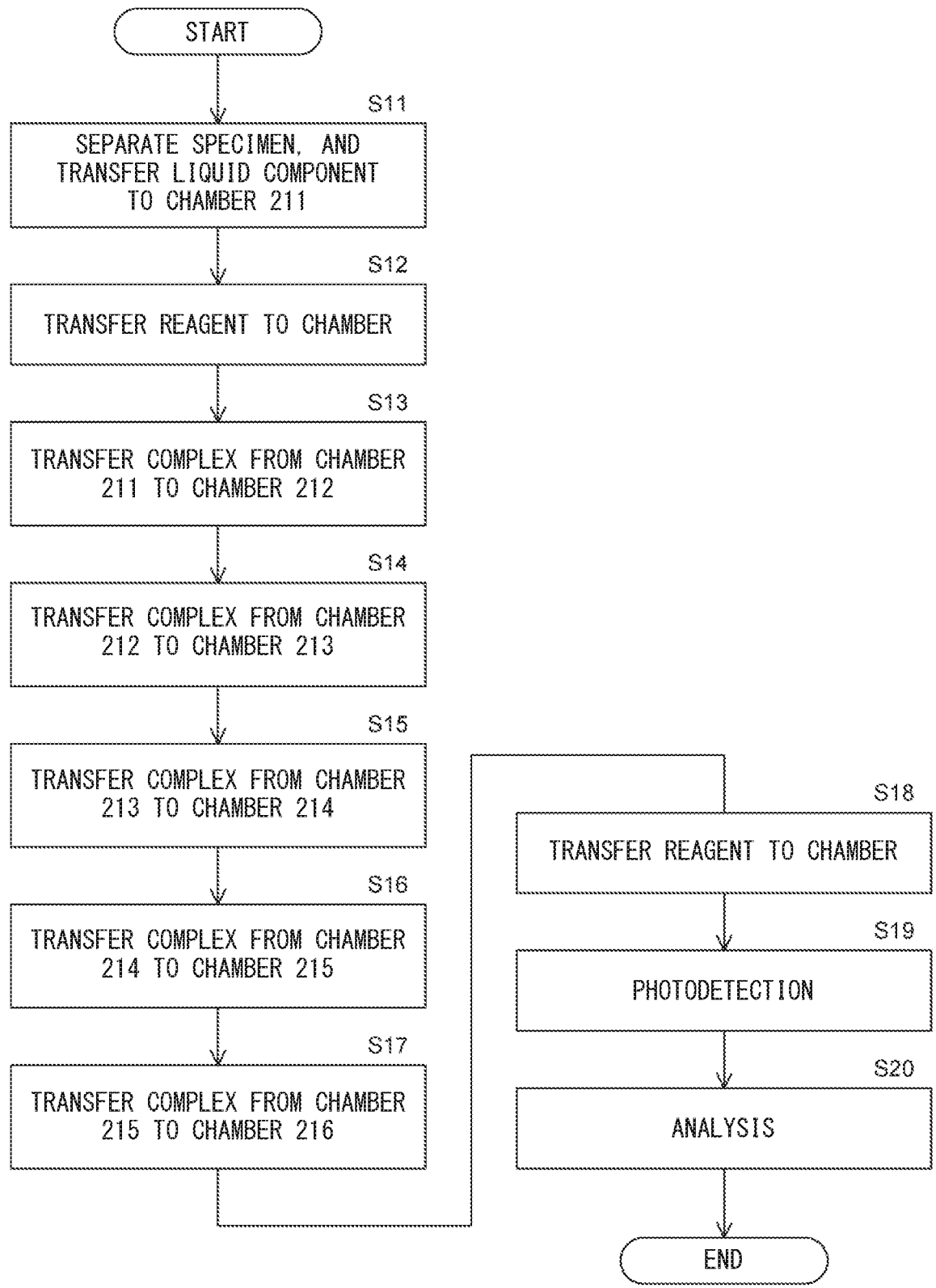
FIG. 9 is a flowchart showing the operation of the measurement apparatus according to the specific configuration example of Embodiment 1.

Upon receiving a start instruction of the operator via the input unit 153, the controller 151 starts process steps shown in FIG. 9. In step S11, the controller 151 causes the specimen in the separator 242 to be separated into a liquid component and a solid component by a centrifugal force, and causes the separated liquid component to be transferred to the chamber 211.

Next, in step S12, the controller 151 causes the reagents stored in the six liquid storage portions 231 on the Y-axis position side, among the seven liquid storage portions 231 shown in FIG. 5B, to be transferred to the chambers 211 to 215, respectively.

Specifically, in step S101 shown in FIG. 10, the controller 151 drives the motor 117 to rotate the liquid-sealed cartridge 200, thereby to locate the seals 232 and 233 arranged in the radial direction, at positions directly beneath the two pressing members 124. Next, in step S102, the controller 151 causes the two pressing members 124 to move downward such that pressing forces are applied to the seals 232 and 233, thereby to open the seals 232 and 233. Thus, as in the cases of FIG. 3C and FIG. 4C, the seals 232 and 233 are inclined in the pressing direction, whereby sealing by the seals 232 and 233 is released.

The controller 151 repeatedly performs the sealing releasing operation as described above to open the six seals 232 and the six seals 233 located in the radial directions of the chambers 211 to 216. Next, in step S103, the controller 151 drives the motor 117 to rotate the liquid-sealed cartridge 200, thereby to transfer, by a centrifugal force, the reagents stored in the six liquid storage portions 231 located in the radial directions of the chambers 211 to 216 to the chambers 211 to 216 via the flow paths 234, respectively.

Thus, the R1 reagent is transferred to the chamber 211, and the liquid component, the R1 reagent, and the R2 reagent are mixed in the chamber 211. The R3 reagent is transferred to the chamber 212, the washing liquid is transferred to the chambers 213 to 215, and the R4 reagent is transferred to the chamber 216.

When transfer of the reagents in step S12 is completed, the controller 151 performs an agitation process. Specifically, the controller 151 drives the motor 117 so as to switch between two different rotation speeds at predetermined time intervals while rotating the motor 117 in a predetermined direction. Thus, an Euler force generated in the rotation direction is changed at the predetermined time intervals, whereby the liquids in the chambers 211 to 216 are agitated. This agitation process is performed not only in step S12 but also in steps S13 to S18 in a similar manner after the transfer process.

The R1 reagent contains a capture substance that binds to the test substance. The capture substance contains, for example, an antibody that binds to the test substance. The antibody is, for example, a biotin-bound HBs monoclonal antibody. The R2 reagent contains magnetic particles and a magnetic particle suspension. The magnetic particles are, for example, streptavidin-bound magnetic particles, the surfaces of which are coated with avidin. In step S12, when the liquid component separated from the specimen, the R1 reagent, and the R2 reagent are mixed and the agitation process is performed, the test substance and the R1 reagent are bound to each other through an antigen-antibody reaction. Then, through a reaction between an antigen-antibody reaction product and the magnetic particles, the test substance bound to the capture substance of the R1 reagent is bound to the magnetic particles via the capture substance. Thus, a complex in which the test substance and the magnetic particles are bound to each other is generated.

Next, in step S13, the controller 151 causes the complex in the chamber 211 to be transferred from the chamber 211 to the chamber 212.

Specifically, the controller 151 drives the motor 117 to rotate the liquid-sealed cartridge 200, thereby to locate the chamber 211 at a position directly above the magnet of the magnetic force applying unit 114. The controller 151 drives the magnetic force applying unit 114 to bring the magnet close to the lower surface of the liquid-sealed cartridge 200, whereby the complex spreading in the chamber 211 is collected by a magnetic force. The controller 151 drives the magnetic force applying unit 114 to move the magnet radially inward, whereby the complex in the chamber 211 is transferred to the arc-shaped region 221 via the region 222. The controller 151 drives the motor 117 to rotate the liquid-sealed cartridge 200, whereby the complex is transferred along the arc-shaped region 221. The controller 151 drives the magnetic force applying unit 114 to move the magnet radially outward, whereby the complex is transferred to the chamber 212 via the region 222. Then, the controller 151 drives the magnetic force applying unit 114 to separate the magnet away from the lower surface of the liquid-sealed cartridge 200.

The process in step S13 is performed as described above. Transfer of the complex in each of steps S14 to S17 is performed in a similar manner to that in step S13.

Thus, the complex generated in the chamber 211 and the R3 reagent are mixed in the chamber 212. The R3 reagent contains a labeling substance. The labeling substance contains: a capture substance that specifically binds to the test substance; and a label. For example, the labeling substance is a labeled antibody in which an antibody is used as a capture substance. In step S13, when the complex generated in the chamber 211 and the R3 reagent are mixed and the agitation process is performed, the complex reacts with the labeled antibody contained in the R3 reagent. Thereby, a complex in which the test substance, the capture antibody, the magnetic particles, and the labeled antibody are combined is generated.

In step S14, the controller 151 causes the complex in the chamber 212 to be transferred from the chamber 212 to the chamber 213. Thereby, the complex generated in the chamber 212 and the washing liquid are mixed in the chamber 213. In step S14, when the complex generated in the chamber 212 and the washing liquid are mixed and the agitation process is performed, the complex and unreacted substance are separated from each other in the chamber 213. That is, in the chamber 213, the unreacted substance is removed by washing.

In step S15, the controller 151 causes the complex in the chamber 213 to be transferred from the chamber 213 to the chamber 214. Thereby, the complex generated in the chamber 212 and the washing liquid are mixed in the chamber 214. Also in the chamber 214, unreacted substance is removed by washing.

In step S16, the controller 151 causes the complex in the chamber 214 to be transferred from the chamber 214 to the chamber 215. Thereby, the complex generated in the chamber 212 and the washing liquid are mixed in the chamber 215. Also in the chamber 215, unreacted substance is removed by washing.

In step S17, the controller 151 causes the complex in the chamber 215 to be transferred from the chamber 215 to the chamber 216. Thereby, the complex generated in the chamber 212 and the R4 reagent are mixed in the chamber 216. The R4 reagent is a reagent for dispersing the complex generated in the chamber 212. The R4 reagent is a buffer solution, for example. In step S17, when the complex generated in the chamber 212 and the R4 reagent are mixed and the agitation process is performed, the complex generated in the chamber 212 is dispersed.

In step S18, the controller 151 causes the R5 reagent to be transferred to the chamber 216. Specifically, the controller 151 executes the processes in steps S101 and S102 shown in FIG. 10, on the seals 232 and 233 of the liquid storage portion 231 located on the Y-axis most negative side, thereby to open the seals 232 and 233. Then, the controller 151 executes the process in step S103 shown in FIG. 10 to transfer the R5 reagent stored in the liquid storage portion 231 located on the Y-axis most negative side, by a centrifugal force, to the chamber 216. Thereby, in the chamber 216, the R5 reagent is further mixed with the mixture generated in step S17.

The R5 reagent is a luminescent reagent containing a luminescent substrate that generates light through a reaction with the labeled antibody bound to the complex. In step S18, when the mixture generated in step S17 and the R5 reagent are mixed and the agitation process is performed, a sample is prepared. This sample causes chemiluminescence when the labeling substance bound to the complex reacts with the luminescent substrate.

In step S19, the controller 151 drives the motor 117 to rotate the liquid-sealed cartridge 200 such that the chamber 216 is located at a position directly above the photodetector of the detector 115, and causes the photodetector to detect light generated from the chamber 216. In step S20, the controller 151 performs an analysis process regarding immunity, on the basis of the light detected by the photodetector of the detector 115. When the photodetector of the detector 115 is implemented by a photo multiplier tube, a pulse wave in response to reception of photons is outputted from the photodetector. The detector 115 counts the photons at regular intervals on the basis of the output signal from the photodetector, and outputs the count value. The controller 151 analyzes whether or not the test substance is present, the amount of the test substance, and the like on the basis of the count value outputted from the detector 115, and causes the display unit 152 to display analysis results.

The measurement apparatus 100 is not limited to the immune analyzer, and may be an apparatus that performs another measurement or analysis. The number of the chambers 211 to 216 and the number of the liquid storage portion 231 are not limited to those described above, and may be changed according to the measurement method. The present disclosure is applicable to various liquid-sealed cartridges for transferring liquids using a centrifugal force.

Embodiment 2

In Embodiment 2, in contrast to Embodiment 1, a projection 56 is formed at the lower surface of the seal 50, and a recess 73 in which the projection 56 is fitted when the seal 50 is inclined by the pressing force F20 is formed at an inner wall of the liquid storage portion 70, as shown in FIGS. 11A and 11B. The other configuration of Embodiment 2 is the same as that of Embodiment 1.

The projection 56 is provided at the center of the lower surface of the seal 50. The projection 56 has a shape obtained by connecting a columnar surface having a fixed diameter to a conical surface having a diameter gradually decreasing toward a tip thereof. In a planar view, the center of the conical surface and the center of the columnar surface are aligned with the center of the seal 50.

The recess 73 is located at a position in which the projection 56 is press-fitted when the projection 56 is inclined by the pressing force F20 of the pressing member D10. An inner wall face at the upper side of the recess 73 has the same shape as an outer wall face of the projection 56 at the outer circumference side of the liquid-sealed cartridge 10. Since the recess 73 is formed in the base plate 20 by die cutting, the lower side of the recess 73 is opened and is covered with the film 40.

When the pressing member D10 moves downward from the state shown in FIG. 11A and the seal 50 is inclined by the pressing force F20, the tip of the projection 56 enters the recess 73. Thereafter, when the pressing member D10 is further pressed downward, the projection 56 is press-fitted in the recess 73 by the pressing force F20, with the connecting portion 52 being slightly stretched. The pressing member D10 presses down the seal 50 until the projection 56 is completely fitted in the recess 73 as shown in FIG. 11B. In the state of FIG. 11B, the seal 50 is pressed such that the outer wall face at the upper side of the projection 56, that is, the outer wall face of the projection 56 at the outer circumference side of the liquid-sealed cartridge 10 in FIG. 11A, is in plane-contact with the inner wall face at the upper side of the recess 73.

According to Embodiment 2, since the projection 56 of the seal 50 is fitted in the recess 73 of the liquid storage portion 70, the seal 50 is maintained in the inclined state as shown in FIG. 11B. Therefore, the seal 50 is prevented from being abruptly closed during liquid transfer, and the sealing-released state can be appropriately maintained.

The shape and the arrangement position of the projection 56 are not limited to those in the configuration example shown in FIGS. 11A and 11B. The projection 56 may have another shape and may be disposed at another position as long as the projection 56 can be press-fitted in the recess 73 by the pressing force F20 of the pressing member D10. The shape and arrangement of the recess 73 are changed according to the shape and arrangement of the projection 56.

Similarly to Embodiment 1, the configuration of Embodiment 2 is also applicable to the liquid-sealed cartridge 200 according to the specific configuration example shown in FIG. 5B. This also applies to Embodiments 3 to 6 described below.

Embodiment 3

In Embodiment 3, in contrast to Embodiment 1, the connection position of the outer peripheral portion of the seal 50 on one side with respect to the center of the seal 50 is shifted in the direction in which the pressing force F20 is applied, relative to the connection position of the other outer peripheral portion of the seal 50 on the other side, as shown in FIG. 12A. More specifically, the connection position of the seal 50 on the opposite side from the rotation shaft R10 is lower than the connection position of the seal 50 on the rotation shaft R10 side. Thereby, the seal 50 is inclined in the direction in which the pressing force F20 is applied. The other configuration of Embodiment 3 is the same as that of Embodiment 1.

In the structure shown in FIG. 12A, when the pressing force F20 is applied to the center of the seal 50 by the pressing member D10, a greater pressing force is applied to the outer peripheral portion of the seal 50 on the rotation shaft R10 side. Therefore, a portion, of the outer peripheral portion of the seal 50, on the rotation shaft R10 side is broken prior to a portion thereof on the opposite side from the rotation shaft R10 and is separated from inner wall face of the liquid storage portion 70, while the portion on the opposite side from the rotation shaft R10 remains connected. Thereby, the seal 50 is inclined as shown in FIG. 12B, and sealing by the seal 50 is released. Thus, according to the configuration of Embodiment 2, since the pressing force F20 applied to the outer peripheral portion of the seal 50 is made uneven, the outer peripheral portion can be smoothly separated at a desired position.

In Embodiment 3, since the outer peripheral portion of the seal 50 is partially broken by making the pressing force applied to the outer peripheral portion of the seal 50 uneven as described above, even when the thickness of the outer peripheral portion is fixed throughout the entire circumference, a portion of the outer peripheral portion can be separated from the liquid storage portion 70, with the other portion thereof remaining connected. Therefore, the outer peripheral portion of the seal 50 may not necessarily have the thick connecting portion 52 and the thin separation portion 53. However, when the connecting portion 52 and the separation portion 53 are provided as in the configuration example shown in FIG. 12A, the separation portion 53 can be more smoothly broken and separated from the liquid storage portion 70, combined with the balance adjustment of the pressing force F20.

The seal 50 may not necessarily be connected to the liquid storage portion 70 such that the portion on the opposite side from the rotation shaft R10 is lowered. For example, the seal 50 may be connected to the liquid storage portion 70 such that the portion on the rotation shaft R10 side is lowered. It is sufficient that the seal 50 is formed such that the position of the outer peripheral portion of the seal 50 to be separated from the liquid storage portion 70 is higher than the other portion. The inclination of the seal 50 can be set according to the position of the outer peripheral portion at which the greater pressing force is to be applied.

The configuration of Embodiment 3 may also be applied to the seal 60. In addition, also in Embodiment 2, the connection position of the outer peripheral portion of the seal 50 may be set as described in Embodiment 3.

Embodiment 4

Figure 13A:
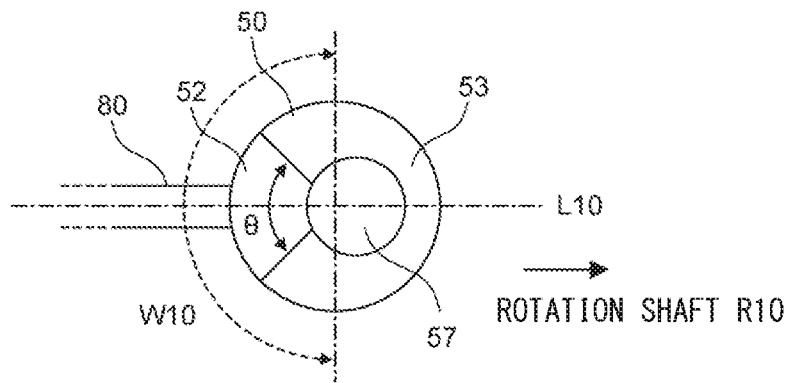
FIG. 13A is a plan view showing the structure of a seal according to Embodiment 4.
Figure 13B:
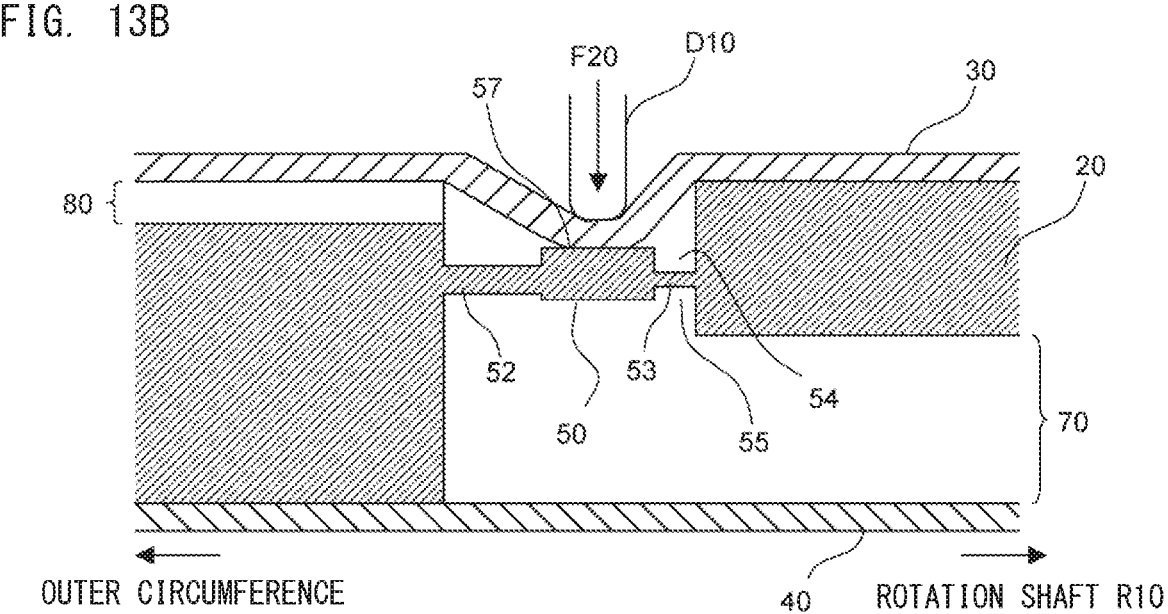
FIG. 13B is a cross-sectional view schematically showing the structures of a seal and a liquid storage portion and a process for opening the seal, according to Embodiment 4.

In Embodiment 4, in contrast to Embodiment 1, a portion-to-be-pressed 57 is provided at a position shifted from the center of the seal 50 in a direction approaching the rotation shaft R10, as shown in FIGS. 13A and 13B. In addition, the upper surface of the portion-to-be-pressed 57 has no recess 51, and is a flat surface. The other configuration of Embodiment 4 is the same as that of Embodiment 1. A recess 51 may be formed at the upper surface of the portion-to-be-pressed 57.

The pressing member D10 is moved downward from a position directly above the portion-to-be-pressed 57. Thereby, the pressing member D10 first contacts with the upper surface of the portion-to-be-pressed 57 via the film 30, and the pressing force F20 is applied to the portion-to-be-pressed 57. The portion-to-be-pressed 57 is a position defining portion that defines the position to which the pressing force F20 of the pressing member D10 is applied. Since the seal 50 is provided with the portion-to-be-pressed 57, the pressing force F20 can be appropriately applied to the seal 50 at a predetermined position.

Figure 13C:
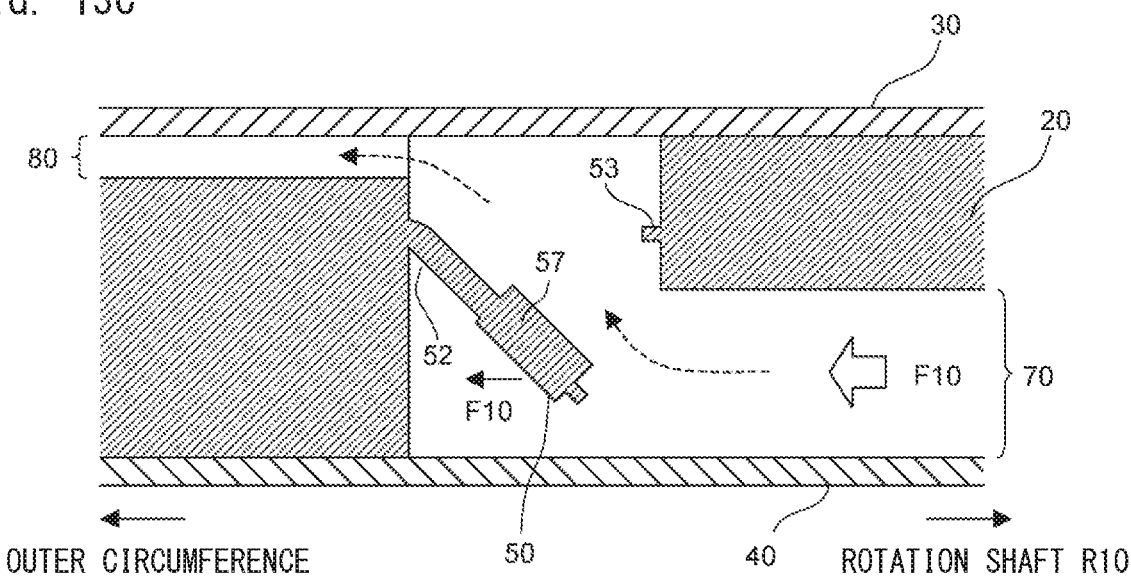
FIG. 13C is a cross-sectional view schematically showing the structures of the seal and the liquid storage portion and the process for opening the seal, according to Embodiment 4.

When the pressing force F20 is applied to the seal 50, a greater pressing force is applied to the outer peripheral portion of the seal 50 on the rotation shaft R10 side. Therefore, as shown in FIG. 13C, the outer peripheral portion on the rotation shaft R10 side is broken by the pressing force, while the outer peripheral portion on the opposite side from the rotation shaft R10 is not broken but remains connected to the liquid storage portion 70. Therefore, when sealing is released, the seal 50 can be inclined in the pressing direction, with a portion thereof remaining connected to the liquid storage portion 70.

Since the seal 50 is inclined with the portion thereof on the opposite side from the rotation shaft R10 remaining connected, when the liquid-sealed cartridge 10 is rotated to transfer the liquid, the centrifugal force F10 is applied to the seal 50 in the direction in which the seal 50 is further inclined. Therefore, the seal 50 is prevented from being abruptly closed during the liquid transfer, and the sealing-released state is appropriately maintained. Therefore, transfer of the liquid to the flow path 80 can be reliably performed.

In Embodiment 4, since the outer peripheral portion of the seal 50 is partially broken by making the pressing force applied to the outer peripheral portion of the seal 50 uneven as described above, even when the thickness of the outer peripheral portion is fixed throughout the entire circumference, a portion of the outer peripheral portion can be separated from the liquid storage portion 70, with the other portion thereof remaining connected. Therefore, the outer peripheral portion of the seal 50 may not necessarily have the thick connecting portion 52 and the thin separation portion 53. However, when the connecting portion 52 and the separation portion 53 are provided as in the configuration example shown in FIGS. 13A and 13B, the separation portion 53 can be more smoothly broken and separated from the liquid storage portion 70, combined with the balance adjustment of the pressing force F20.

The portion-to-be-pressed 57 may not necessarily be displaced from the center of the seal 50 along one diameter L10 of the liquid-sealed cartridge 10 as shown in FIG. 13A. It is sufficient that the portion-to-be-pressed 57 is displaced in a direction approaching a position of the outer peripheral portion to which a greater pressing force is to be applied. The portion-to-be-pressed 57 may be disposed at a position shifted not only in the direction along the diameter L10 but also in another direction approaching the rotation shaft R10 from the center of the seal 50.

The configuration of Embodiment 4 may also be applied to the seal 60. In addition, also in Embodiments 2 and 3, the configuration of displacing a portion-to-be-pressed 57 from the center of the seal 50 may be used as described in Embodiment 4.

Embodiment 5

In Embodiment 5, in contrast to Embodiment 1, a projection 58 is provided at the upper surface of the seal 50 as shown in FIGS. 14A and 14B. The upper surface of the projection 58 has no recess 51, and is a flat surface. The other configuration of Embodiment 5 is the same as that of Embodiment 1. A recess 51 may be formed at upper surface of the projection 58.

The projection 58 has a columnar shape. The projection 58 may have another shape, such as a rectangular column shape or a shape having a diameter gradually decreasing toward a tip thereof. The projection 58 is disposed at a position displaced in a direction approaching the rotation shaft R10 with respect to the center of the seal 50. The arrangement position of the projection 58 is not limited thereto, and may be the center of the seal 50.

By providing the projection 58 as described above, the pressing member D10 first contacts with the projection 58, and applies the pressing force to the position of the projection 58. Therefore, the pressing force can be appropriately applied to the seal 50 at a predetermined position.

When the projection 58 is displaced in the direction approaching the rotation shaft R10 with respect to the center of the seal 50 as shown in FIGS. 14A and 14B, a greater pressing force is applied to a portion, on the rotation shaft R10 side, of the outer peripheral portion of the seal 50, as in Embodiment 4 described above. In this case, as in Embodiment 3 described above, even when the thickness of the outer peripheral portion of the seal 50 is fixed throughout the entire circumference, the outer peripheral portion on the rotation shaft R10 side is broken while the outer peripheral portion on the opposite side from the rotation shaft R10 is not broken but remains connected to the liquid storage portion 70, due to the difference in the pressing force. Therefore, in the configuration shown in FIGS. 14A and 14B, the outer peripheral portion of the seal 50 may not necessarily have the thick connecting portion 52 and the thin separation portion 53. However, when the connecting portion 52 and the separation portion 53 are provided as in the configuration example of FIGS. 14A and 14B, the separation portion 53 can be more smoothly broken and separated from the liquid storage portion 70.

The configuration of Embodiment 5 may also be applied to the seal 60. In addition, also in the other embodiments, a projection 58 may be provided at the upper surface of the seal 50, as in Embodiment 5.

Embodiment 6

Figure 15A:
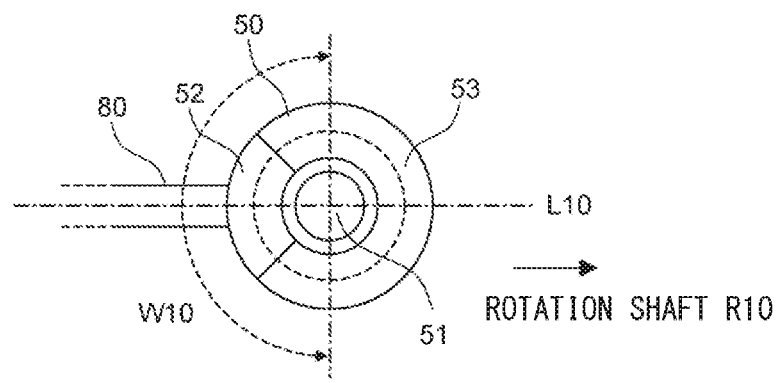
FIG. 15A is a plan view showing the structure of a seal according to Embodiment 6.
Figure 15B:
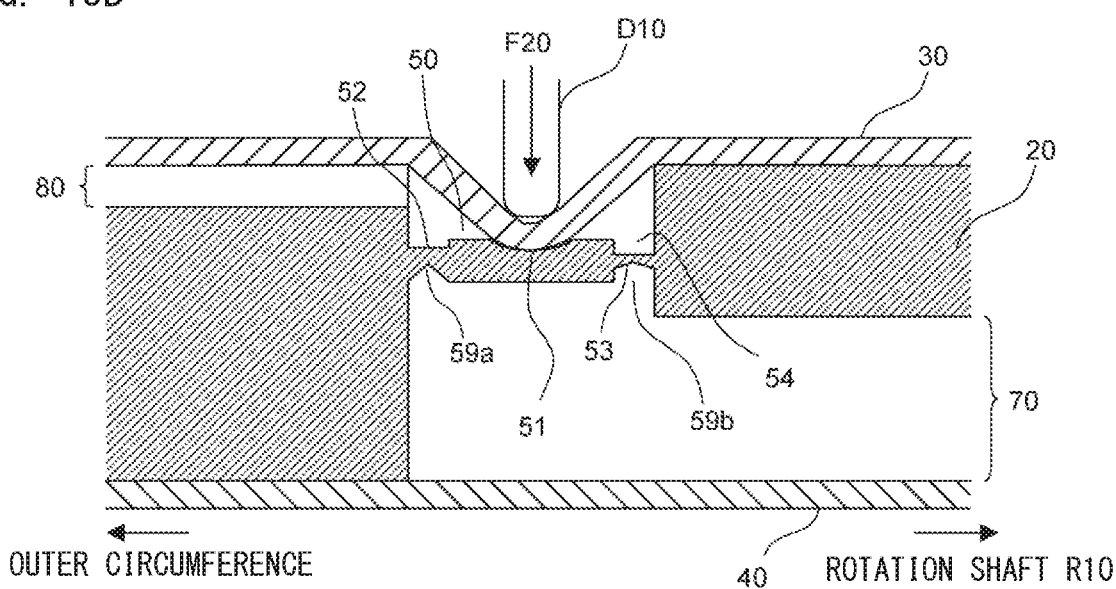
FIG. 15B is a cross-sectional view schematically showing the structures of the seal and a liquid storage portion and a process for opening the seal, according to Embodiment 6.

In Embodiment 6, in contrast to Embodiment 1, the recessed groove 55 formed at the lower surface of the seal 50 is replaced with recessed grooves 59a and 59b as shown in FIGS. 15A and 15B. That is, in Embodiment 1, the recessed groove 55 has a rectangular cross-sectional shape. In contrast to Embodiment 1, in Embodiment 6, the recessed groove 59a provided at the lower surface of the connecting portion 52 has a V-shaped cross-section, and the recessed groove 59b provided at the lower surface of the separation portion 53 has a V-shaped cross-section. The other configuration of Embodiment 5 is the same as that of Embodiment 1.

In FIG. 15A, a broken line that orbits the positions of the connecting portion 52 and the separation portion 53 indicates a ridge line of the recessed grooves 59a and 59b.

The bottom of the cross-section of each of the recessed grooves 59a and 59b may not necessarily be angular, and may be rounded. In addition, two oblique faces forming the bottom of each of the recessed grooves 59a and 59b may not necessarily be flat faces. Both or one of the two oblique faces may be curved faces. It is sufficient that each of the recessed grooves 59a and 59b has a width gradually decreasing toward the bottom.

Figure 15C:
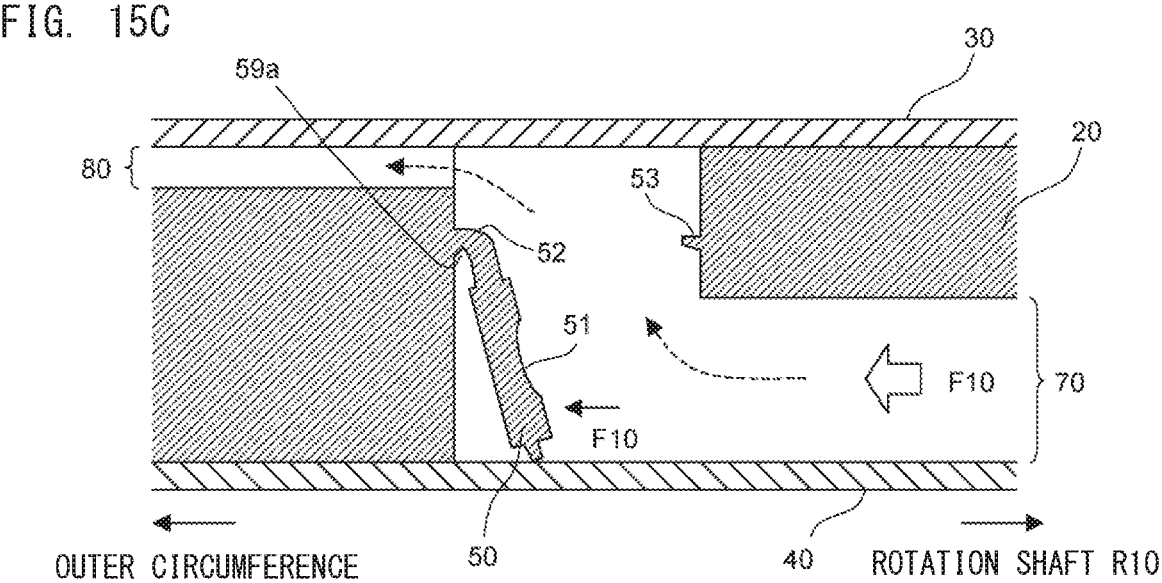
FIG. 15C is a cross-sectional view schematically showing the structures of the seal and the liquid storage portion and the process for opening the seal, according to Embodiment 6.
Figure 17:
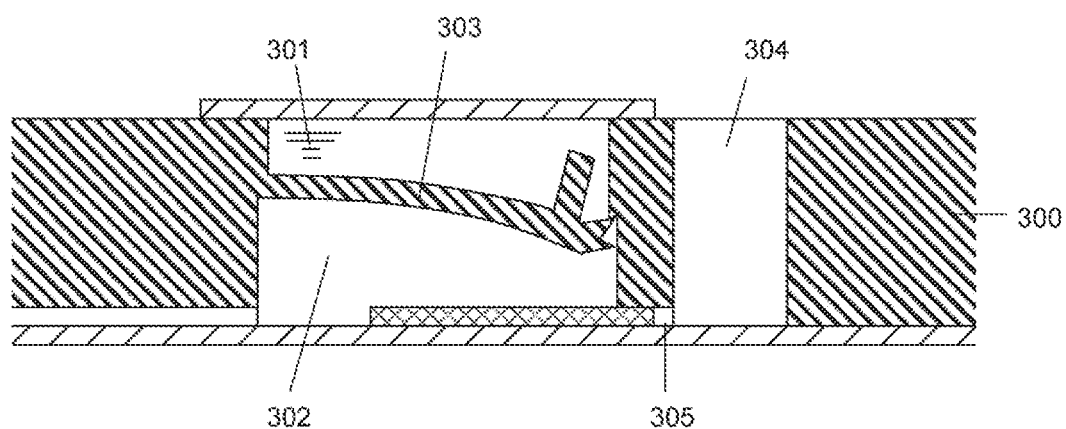
FIG. 17 shows the structure of the conventional art.

By providing the recessed grooves 59a and 59b each having the V-shaped cross-section, the seal 50 is supported more flexibly at the connecting portion 52. Therefore, as shown in FIG. 15C, the seal 50 can be greatly inclined by applying the pressing force F20 thereto. Furthermore, since the seal 50 is supported more flexibly by the connecting portion 52, the seal 50, after sealing is released, hardly return to the position before the sealing release. Therefore, the sealing-released state can be maintained more stably.

In addition, since the outer peripheral portion of the seal 50 is broken at the apex of the V shape, the broken face is stable and smooth. Therefore, flow of the liquid from the liquid storage portion 70 to the flow path 80 is stabilized.

A recessed groove having a V-shaped cross-section may be further provided at each of the upper surfaces of the connecting portion 52 and the separation portion 53. Alternatively, a recessed groove having a V-shaped cross-section may be provided not at the lower surfaces of the connecting portion 52 and the separation portion 53 but at the upper surfaces of the connecting portion 52 and the separation portion 53.

The thick connecting portion 52 may not be provided with a recessed groove having a V-shaped cross-section. In this case, the outer peripheral portion of the seal 50 can be reliably broken at the position of the apex of the V-shaped recessed groove provided in the separation portion 53.

The configuration of Embodiment 6 may also be applied to the seal 60. In addition, also in the other embodiments, a recessed groove having a V-shaped cross-section may be provided in a region of the connecting portion 52 and the separation portion 53, as in Embodiment 6.

Embodiment 7

The seal 50, in a plan view, may not necessarily have a round shape, but may have another shape. For example, as shown in FIGS. 16A and 16B, the shape of the seal 50 in a planar view may be a shape obtained by combining a semicircle and an isosceles triangle. That is, the separation portion 53 may have a shape having a pointed end. The other configuration of Embodiment 7 is the same as that of Embodiment 1.

When the separation portion 53 has such a shape, the pressing force F20 is concentrated on the pointed end portion, and a start point of breaking is more likely to occur in this portion. Therefore, the separation portion 53 can be broken to incline the seal 50 with a smaller pressing force F20. Accordingly, the driving mechanism of the pressing member 20 can be downsized.

The pointed end of the separation portion 53 may not necessarily be located on the rotation shaft R10 side, and may be located at any position to be a start point of breaking. In addition, the pointed end may not necessarily have a shape formed by two straight lines intersecting each other in a planar view, and may have a shape formed by two curved-lines intersecting each other or a shape formed by a straight line and a curved line intersecting each other. The shape of the recess 21 shown in FIG. 2 is changed according to the shape of the seal 50.

The configuration of Embodiment 7 may also be applied to the seal 60. In addition, also in the other embodiments, the separation portion 53 may have a shape having a pointed end in a planar view, as in Embodiment 7.

Embodiment 8

The connecting portion 52 may not necessarily have a sector shape in a planar view. For example, as shown in FIG. 16C, two boundaries between the connecting portion 52 and the separation portion 53 may be parallel to each other in a planar view. The other configuration of Embodiment 8 is the same as that of Embodiment 1.

The configuration of Embodiment 8 may also be applied to the seal 60. In addition, also in the other embodiments, as in Embodiment 8, the shape of the connecting portion 52 in a planar view can be variously changed. For example, two boundaries between the connecting portion 52 and the separation portion 53 may be parallel to each other in a planar view.

What is claimed is:
1. A liquid-sealed cartridge comprising:
a base plate having a first opening and a second opening;
a liquid storage formed between a lower surface of the base plate and an upper surface of a second film, the liquid storage storing a liquid;
a first seal sealing the first opening;
a second seal sealing the second opening;
a first film provided on an upper surface of the base plate and elastically formed to press each of the first seal and the second seal; and
the second film provided on the lower surface of the base plate,
wherein each of the first seal and the second seal comprising:
a connector connected to the base plate; and
a separator connected to the base plate, and
wherein a thickness of the separator is less than a thickness of the connector;
wherein the separator is configured to be disconnected from the base plate when the first film presses each of the first seal and the second seal, and
wherein the first opening and the second opening are in communication through the liquid storage when the separator is disconnected from the base plate.
2. The liquid-sealed cartridge of claim 1, wherein, the first film is configured to press each of the first seal and the second seal such that the connector remains connected to the base plate and the separator is disconnected from the base plate.

3. The liquid-sealed cartridge of claim 1, wherein:
the connector includes a first groove that is provided at a lower surface of the connector, wherein a thickness of a center of the connector is less than a thickness of ends of the connector, and
the separator includes a second groove that is provided at a lower surface of the separator, wherein a thickness of a center of the separator is less than a thickness of ends of the separator.

4. The liquid-sealed cartridge of claim 1, wherein a recess is formed at a center position of an upper surface of the first seal and the second seal.

5. The liquid-sealed cartridge of claim 1, wherein:
the thickness of the separator is greater than or equal to $1/12$ of the thickness of the connector, and
the thickness of the separator is less than or equal to $5/12$ of the thickness of the connector.

6. The liquid-sealed cartridge of claim 1, wherein
a projection is provided at a lower surface of the first seal, and
a recess is provided at an inner wall of the liquid storage, wherein the projection is configured to be fitted into the recess.

7. The liquid-sealed cartridge of claim 1, wherein the liquid storage is configured to transfer the stored liquid upon rotation of the liquid-sealed cartridge at a speed of 100 revolutions per minute (rpm) to 10,000 rpm.

8. The liquid-sealed cartridge of claim 1, wherein the second film is not elastically formed.

9. The liquid-sealed cartridge of claim 1, wherein
a projection is provided at a lower surface of the second seal, and
a recess is provided at an inner wall of the liquid storage, wherein the projection is configured to be fitted into the recess.

* * * * *